United States Patent [19]

Raddatz et al.

[11] Patent Number: 4,829,053
[45] Date of Patent: May 9, 1989

[54] AMINO ACID DERIVATIVES

[75] Inventors: Peter Raddatz; Joachim Gante, both of Darmstadt; Claus J. Schmitges, Gross-Umstadt; Klaus Otto Minck, Ober-Ramstadt; Johannes Sombroek, Darmstadt; Günter Hölzemann, Seehim, all of Fed. Rep. of Germany

[73] Assignee: Merck Patent Gesellschaft Mit Beschränkter Haftung, Darmstadt, Fed. Rep. of Germany

[21] Appl. No.: 80,265

[22] Filed: Jul. 31, 1987

[30] Foreign Application Priority Data

Aug. 1, 1986 [DE] Fed. Rep. of Germany ....... 3626130

[51] Int. Cl.$^4$ .................. A61K 37/43; C07K 5/06; C07K 5/08; C07D 211/70
[52] U.S. Cl. .................................... 514/18; 546/336; 548/251; 548/253; 548/205; 514/381; 514/194; 514/195; 514/372; 514/19; 530/331
[58] Field of Search .............. 530/330, 331; 514/18, 514/381, 194, 195, 372; 546/336; 548/251, 253, 205

[56] References Cited

U.S. PATENT DOCUMENTS

| | | | |
|---|---|---|---|
| 4,705,846 | 11/1987 | Thaisrivongs | 530/331 |
| 4,719,288 | 1/1988 | Fuhrer et al. | 546/336 |
| 4,721,776 | 1/1988 | Raddatz et al. | 530/330 |
| 4,725,580 | 2/1988 | Wagnon et al. | 530/332 |
| 4,727,060 | 2/1988 | Bühlmayer et al. | 514/18 |

FOREIGN PATENT DOCUMENTS

| | | |
|---|---|---|
| 0077028 | 4/1983 | European Pat. Off. . |
| 0081783 | 6/1983 | European Pat. Off. . |
| 0184855 | 6/1986 | European Pat. Off. . |
| 84/03044 | 8/1984 | PCT Int'l Appl. . |

Primary Examiner—Delbert R. Phillips
Attorney, Agent, or Firm—Millen & White

[57] ABSTRACT

New aminoacid derivatives of the formula I

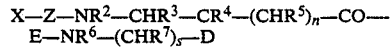

wherein X, Z, $R^2$, $R^3$, $R^4$, $R^5$, E, $R^6$, $R^7$, D, n and s have the meanings defined herein and their salts, inhibit the activity of human plasma renin.

18 Claims, No Drawings

AMINO ACID DERIVATIVES

BACKGROUND OF THE INVENTION

The invention relates to new amino acid derivatives. Similar compounds are disclosed in EP-A 77,028, EP-A-81,783 and EP-A-184,855.

SUMMARY OF THE INVENTION

It is an object of this invention to provide new compounds having valuable properties, in particular compounds which can be used for the preparation of medicaments.

Upon further study of the specification and appended claims, further objects and advantages of this invention will become apparent to those skilled in the art.

These objects have been achieved by providing new amino acid derivatives of the formula I $$X-Z-NR^2-CHR^3-CR^4-(CHR^5)_n-CO-E-NR^6-(CHR^7)_s-D \quad\quad I$$

wherein
X is H, $R^1-O-C_mH_{2m}-CO-$, $R^1-C_mH_{2m}-O-CO-$, $R^1-C_mH_{2m}-CO-$, $R^1-SO_2-$ or $(R^1-C_mH_{2m})-L(R^1-C_pH_{2p})-C_rH_{2r}-CO-$,
Z is 0 to 4 aminoacid radicals attached to one another by a peptide linkage and selected from the group consisting of Abu, Ada, Ala, Arg, Asn, Asp, Bia, Cal, Dab, Gln, Glu, His, N(im)-alkyl-His, Ile, Leu, tert.-Leu, Lys, Met, αNal, βNal, Nbg, Nle, Orn, Phe, Pro, Ser, Thr, Tic, Trp, Tyr and Val,
E is 0 to 2 amino acid radicals attached to one another by a peptide linkage and selected from the group consisting of Abu, Ala, Cal, His, Ile, Leu, Met, Nle, Phe, Trp, Tyr and Val,
D is a tetrazolyl group which is unsubstituted or substituted by A or a thiazolyl group which is substituted by $H_2N$, HAN, $A_2N$, $R^8-CO-NH-$, $R^9-NH-CO-NH-$, $R^{10}-NH-CS-NH-$, $R^{11}OOC-$, $R^{12}R^{13}N-CO-$ or CN,
$R^1$, $R^3$, $R^7$, $R^8$, $R^9$, $R^{10}$, $R^{11}$, $R^{12}$ and $R^{13}$ are each H, A, Ar, Ar-alkyl, Het, Het-alkyl, cycloalkyl which has 3-7 C atoms and is unsubstituted or monosubstituted or polysubstituted by A, AO and.or Hal, cycloalkylalkyl having 4-11 C atoms, bicycloalkyl or tricyloalkyl having in each case 7-14 C atoms or bicycloalkylalkyl or tricycloalkylalkyl having in each case 8-8 C atoms,
$R^2$, $R^5$, and $R^6$ are each H or A,
$R^4$ is (H, OH), (H, $NH_2$) or $=O$,
L is CH or N,
m, p and r are each 0, 1, 2, 3, 4 or 5,
n is 1 or 2,
s is 0, 1 or 2,
Ar is phenyl which is unsubstituted or monosubstituted or polysubstituted by A, AO, Hal, $CF_3$, OH and/or $NH_2$ or is unsubstituted naphthyl,
Het is saturated or unsaturated, 5-membered or 6-membered, heterocyclic radical which is 1-4 N, O and/or S atoms, and which can be condensed with a benzene ring and/or monosubstituted or polysubstituted by A, AO, Hal, $CF_3$, HO, $O_2N$, carbonyl oxygen, $H_2N$, HAN, $A_2N$, AcNH, AS, ASO, $ASO_2$, AOOC, CN, $H_2NCO$, $H_2NSO_2$, $ASO_2NH$, Ar, Ar-alkenyl, hydroxyalkyl and/or aminoalkyl, having in each case 1-8 C atoms, and/or the N and/or S heteroatoms thereof independently being optionally oxidized,
Hal is F, Cl, Br or I,
Ac is $A-CO-$, $Ar-CO-$ or $A-NH-CO-$ and
A is alkyl having 1-8 C atoms, and
wherein one or more $-N(alkyl)-CO-$ groups can also be present instead of one or more $-NH-CO-$ groups, and also salts thereof.

Typically, all alkyl portions mentioned above have up to 8 C atoms, including alkenyl groups and the alkyl portions of Ar-alkyl and Het-alkyl. The cycloalkylalkyl, bicycloalkyl and tricycloalkyl groups can optionally also be substituted by $C_{1-4}$-alkyl.

In the foregoing, selection of variables defined together is made independently.

It has been found that the compounds of the formula I and their salts possess very valuable properties. Above all, they inhibit the activity of humam plasma renin. This action can be demonstrated, for example, by the method of F. Fyhrquist et al., Clin. Chem. 22, 250-256 (1976). It is noteworthy that these compounds are very specific inhibitors of renin; as a rule appreciably higher concentrations of these compounds are required for the inhibition of other aspartylproteinases (for example pepsin and cathepsin D), concentrations about 100 to 10,000 times as high.

The compounds can be employed as active compounds for medicaments in human and verterinary medicine, in particular for the prophylaxis and treatment of cardiac, circulatory and vascular diseases, above all hypertension, cardiac insufficiency and hyperaldosteronism. In addition, the compounds can be used for diagnostic purposes in order to determine, in patients having hypertension or hyperaldosteronism, the possible contribution of renin activity towards maintaining the pathological condition. Diagnostic tests of this type can be carried out in the manner described in European Pat. No. A-77,028.

The invention also relates to a process for the preparation of an aminoacid derivative of the formula I and also salts thereof, characterized in that it is set free from one of its functional derivatives by treatment with a solvolyzing or hydrogenolyzing agent, or a compound which corresponds to the formula I, but contains one or more additional C—C— and/or C—N— and/or C—O— bonds and/or O atoms instead of H atoms is reduced, or a carboxylic acid of the formula II $$X-G^1-OH \quad\quad II$$

wherein
$G^1$ is
(a) $Z^1$,
(b) Z,
(c) Z—W,
(d) Z—W—$E^1$, or
(e) Z—W—E, and
W is $-NR^2-CHR^3-CR^4-(CHR^5)_n-CO-$
is reacted with an amino compound of the formula III $$H-G^2 \quad\quad III$$

wherein
$G^2$ is
(a) $-Z^2-W-E-NR^6-(CHR^7)_s-D$,
(b) $-W-E-NR^6-(CHR^7)_s-D$,
(c) $-E-NR^6-(CHR^7)_s-D$,
(d) $-E^2-NR^6-(CHR^7)_s-D$,
(e) $-NR^6-(CHR^7)_s-D$, $E^1+E^2$ together are E and
$Z^1+Z^2$ together are Z, and,
in a compound of the formula I, if appropriate, a functionally modified amino and/or hydroxyl group is liberated by treatment with solvolyzing or hydrogenolyzing agents and/or, in order to prepare a compound of the formula I in which $R^4$=(H, OH) or (H, NH$_2$), an aminoketo-acid derivative of the formula I in which $R^4$=O is reduced or reductively aminated, and/or a radical D is converted into another radical D by treatment with esterifying, solvolyzing or amidizing agents, and/or a compound of the formula I is converted into one of its salts by treatment with an acid.

The abbreviations of aminoacid radicals listed above and below represent the radicals —NR—CR'R"—CO— (wherein R,R' and R" have the specific meanings known for each aminoacid) or the following aminoacids:

Abu: 2-aminobutyric acid
Ada: adamanthylalanine
Ala: alanine
Arg: arginine
Asn: asparagine
Asp: aspartic acid
Bia: benzimidazolylalanine
Cal: cyclohexylalanine
Dab: 2,4-diaminobutyric acid
Gln: glutamine
Glu: glutamic acid
His: histidine
N(im)-alkyl-His: histidine substituted in the 1-position of the imidazole ring by A
Ile: isoleucine
Leu: leucine
tert.-leu: tert.-leucine
Lys: lysine
Met: methionine
αNal: α-naphthylalanine
βNal: β-naphthylalanine
Nbg: (2-norbornyl)-glycine
Nle: norleucine
N-Me-His: N-methylhistidine
N-Me-Phe: N-methylphenylalanine
Orn: ornithine
Phe: phenylalanine Pro: proline
Ser: serine
Thr: threonine
Tic: tetrahydroisoquinoline-1-carboxylic acid
Trp: tryptophan
Tyr: tyrosine
val: valine.
Also the following abbreviations are used hereinafter:
BOC: tert.-butoxycarbonyl
imi-BOM: benzyloxymethyl in the 1-position of the imidazole ring
CBZ: benzyloxycarbonyl
DNP: 2,4-dinitrophenyl
imi-DNP: 2,4-dinitrophenyl in the 1-position of the imidazole ring
ETNC: N-ethylcarbamoyl
ETOC: ethoxycarbonyl
FMOC: 9-fluorenylmethoxycarbonyl
IPNC: N-isopropylcarbamoyl
IPOC: isopropoxycarbonyl
MC: morpholinocarbonyl
OMe: methyl ester
OEt: ethyl ester
PBB: 4-phenyl-2-benzylbutyryl
POA: phenoxyacetyl
DCCI: dicyclohexylcarbodiimide
HOBt: 1-hydroxybenzotriazole.

Insofar as the aminoacids mentioned above can exist in several enantiomeric forms, in the preceding and following text all these forms and also mixtures thereof (for example the DL-forms) are included, for example as a constituent of the compounds of the formula I. The L-forms are preferred. Where individual compounds are listed below, the abbreviations of these aminoacids relate in each case to the L-form, unless anything to the contrary is expressly indicated.

In the preceding and following text, the radicals and/or parameters X, Z, E, D, $R^1$ to $R^{13}$, L, m, n, p, r, s, Ar, Het, Hal, Ac, A, $G^1$, $G^2$, $E^1$, $E^2$, $Z^1$, $Z^2$ and W have the meanings indicated in the formula I, II or III, unless anything to the contrary is expressly indicated. If two radicals $R^1$, $R^5$ and/or $R^7$ are present in a compound of the formula I, they can be identical or different from one another.

In the above formulae, A and the other alkyl portions have 1-8, preferably 1, 2, 3 or 4, C atoms. A is preferably methyl and also ethyl, propyl, isopropyl, butyl, isobutyl, sec.-butyl or tert.-butyl, and also pentyl, 1-, 2- or 3-methylbutyl, 1,1-, 1,2- or 2,2-dimethylpropyl, 1-ethylpropyl, hexyl, 1-, 2-, 3- or 4-methyl-pentyl, 1,1-, 1,2-, 1,3-, 2,2-, 2,3- or 3,3-dimethylbutyl, 1-ethylbutyl, 2-ethylbutyl, 1-ethyl-1-methylpropyl, 1-ethyl-2-methylpropyl, 1,1,2-trimethylpropyl, 1,2,2-trimethylpropyl, heptyl or octyl.

Cycloalkyl is preferably cyclopropyl, cyclobutyl, cyclopentyl, cyclohexyl or cyclopheptyl, but also, for example, 1-, 2- or 3-methylcyclopentyl or 1-, 2-, 3- or 4-methylcyclohexyl.

Accordingly, cycloalkylalkyl is preferably cyclopropylmethyl, 2-cyclopropylethyl, cyclobutylmethyl, 2-cyclobutylethyl, cyclohexylmethyl or 2-cyclohexylethyl, but also, for example, 1- , 2- or 3-methylcyclopentylmethyl or 1-, 2-, 3- or 4-methylcyclohexylmethyl.

Bicycloalkyl is preferably 1-decalyl, 2-decalyl, 2-bicyclo[2,2,1]heptyl or 6,6-dimethyl-2-bicyclo[3,1,1]heptyl.

Tricycloalkyl is preferably 2-adamantyl.

Hal is preferably F, Cl or Br, but also I.

Ac is preferably A—CO—, such as acetyl, propionyl or butyryl, AR—CO—, such as benzoyl, o-, m- or p-methoxybenzoyl or 3,4-dimethoxybenzoyl, or A—NH—CO—, such as N-methylcarbamoyl or N-ethylcarbamoyl.

Ar is preferably pheny, but also, preferably, o-, m- or p-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, o-, m- or p-hydroxyphenyl, 2,3-, 2,4-, 2,5-, 2,6-, 3,4- or 3,5-dimethoxyphenyl, 3,4,5-trimethoxyphenyl, o-, m- or p-aminophenyl or 1-naphthyl or 2-naphthyl.

Accordingly, Ar-alkyl is preferably benzyl, 1-phenylethyl, 2-phenylethyl, o-, m- or p-methoxybenzyl, 1-o-, 1-m- or 1-p-tolylethyl, 2-o-, 2-m- or 2-p-tolylethyl, o-, m- or p-ethylbenzyl, 1-o-, 1-m- or 1-p-ethylphenylethyl, 2-o-, 2-m- or 2-p-ethylphenylethyl, o-, m- or p-methoxybenzyl,1-o-, 1-m- or 1-p-methoxyphenylethyl, 2-o-, 2-m- or 2-p-methoxyphenylethyl, o-, m- or p-fluorobenzyl, 1-o-, 1-m- or 1-p-fluorophenylethyl, 2-o-, 2-m- or 2-p-fluorophenylethyl, o-, m- or p-chlorobenzyl, 1-o-, 1-m- or 1-p-chlorophenylethyl, 2-o-, 2-m- or 2-p-chlorophenylethyl, o-, m- or p-bromobenzyl, 1-o-, 1-m- or 1-p-bromophenylethyl, 2-o-, 2-m- or 2-p-bromophenylethyl, o-, m- or p-iodobenzyl, 1-o-, 1-m- or 1-p-iodophenylethyl, 2-o-, 2-m- or 2-p-iodophenylethyl, o-, m- or p-trifluoromethylbenzyl, o-, m- or p-hydroxybenzyl, 2,3-, 2,4-, 2,5-, 2,6-, 3,4- or 3,5-dimethoxybenzyl, 3,4,5-trimethoxybenzyl, o-, m- or p-aminobenzyl or 1-naphthylmethyl or 2-naphthylmethyl.

Het is preferably 2-furyl, 3-furyl, 2-thienyl, 3-thienyl, 1-, 2- or 3-pyrryl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidyl, and also, preferably, 1,2,3-triazol-1-, -4- or -5-yl, 1,2,4-triazol-1-, -3- or -5-yl, 1-tetrazolyl, 5-tetrazolyl, 1,2,3-oxadiazol-4-yl, 1,2,3-oxadiazol-5-yl, 1,2,4-oxadiazol-3-yl, 1,2,4-oxadiazol-5-yl, 1,3,4-thiadiazol-2-yl, 1,3,4-thiadiazol-5-yl, 1,2,4-thiadiazol-3-yl, 1,2,4-thiadiazol-5-yl, 2,1,5-thiadiazol-3-yl, 2,1,5-thiadiazol-4-yl, 2-, 3-, 4-, 5- or 6-2H-thiopyranyl, 2-, 3- or 4-4H-thiopyranyl, 3-pyridazinyl or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 3-, 4-, 5-, 6- or 7-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7-, or 8-quinolyl, 1-, 3-, 4-, 5-, 6-, 7- or 8-isoquinolyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolyl, 2-, 4-, 5-, 6-, 7- or 8-quinazolyl. The heterocyclic radicals can also be partly or completely hydrogenated. Het can, therefore, also be, for example, 2,3-dihydro-2-, -3-, -4- or -5-furyl, 2,5-dihydro-2-, -3-, -4- or 5-furyl, tetrahydro-2-furyl, tetrahydro-3-furyl, tetrahydro-2-thienyl, tetrahydro-3-thienyl, 2,3-dihydro-1-, -2-, -3-, -4- or -5-pyrryl, 2,5-dihydro-1-, -2-, -3-, -4- or -5-pyrryl, 1-, 2- or 3-pyrrolidinyl, tetrahydro-1-, -2- or -4-imidazolyl, 2,3-dihydro-1-, -2-, -3-, -4- or 5-pyrazolyl, 2,5-dihydro-1-, -2-, -3-, -4- or 5-pyrazolyl, tetrahydro-1-, -3-, or -4-pyrazolyl, 1,4-dihydro-1-, 2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidyl, 1-, 2- or 3-piperazinyl, 1,2,3,4-tetrahydro-1-, -2-, -3-, -4-, -5-, -6-, -7-, or -8-quinolyl, 1,2,3,4-tetrahydro-1-, -2-, -3-, -4-, -5-, -6-, -7- or 8-isoquinolyl.

The heterocyclic radicals can also be substituted as indicated. Het can, therefore, also be, preferably: 2-amino-4-thiazolyl, 4-carboxy-2-thiazolyl, 4-carbamoyl-2-thiazolyl, 4-(2-aminoethyl)-2-thiazolyl, 2-amino-5,6-dimethyl-3-pyrazinyl, 4-carbamoylpiperidino and also, for example, 3-, 4- or 5-methyl-2-furyl, 2-, 4- or 5-methyl-3-furyl, 2,4-dimethyl-3-furyl, 5-nitro-2-furyl, 5-styryl-2-furyl, 3-, 4- or 5-methyl-2-thienyl, 2-, 4- or 5-methyl-3-thienyl, 3-methyl-5-tert.-butyl-2-thienyl, 5-chloro-2-thienyl, 5-phenyl-2-thienyl, 5-phenyl-3-thienyl, 1-, 3-, 4- or 5-methyl-2-pyrryl, 1-methyl-4-nitro-2-pyrryl, 1-methyl-5-nitro-2-pyrryl, 3,5-dimethyl-4-ethyl-2-pyrryl, 4-methyl-5-pyrazolyl, 4-methyl-2-thiazolyl, 5-methyl-2-thiazolyl, 2-methyl-4-thiazolyl, 5-methyl-4-thiazolyl, 2-methyl-5-thiazolyl, 4-methyl-5-thiazolyl, 2,4-dimethyl-5-thiazolyl, 3-, 4-, 5- or 6-methyl-2-pyridyl, 2-, 4-, 5- or 6-methyl-3-pyridyl, 2-methyl-4-pyridyl, 3-methyl-4-pyridyl, 3-, 4-, 5- or 6-chloro-2-pyridyl, 2-, 4-, 5- or 6-chloro-3-pyridyl, 2-chloro-4-pyridyl, 3-chloro-4-pyridyl, 2,6-dichloropyridyl, 2-hydroxy-3-, -4-, -5- or -6-pyridyl (=1H-2-pyridon-3-, -4-, -5- or -6-yl), 5-phenyl-1H-2-pyridon-3-yl, 5-p-methoxyphenyl-1H-2-pyridon-3-yl, 2-methyl-3-hydroxy-4-hydroxymethyl-5-pyridyl, 2-hydroxy-4-amino-6-methyl-3-pyridyl, 3-N'-methylureido-1H-4-pyridon-5-yl, 5- or 6-methyl-4-pyrimidyl, 2,6-dihydroxy-4-pyrimidyl, 5-chloro-2-methyl-4-pyrimidyl, 2-methyl-4-amino-5-pyrimidyl, 3-methyl-2-benzofuryl, 2-ethyl-3-benzofuryl, 7-methyl-2-benzothienyl, 1-, 2-, 4-, 5-, 6- or 7-methyl-3-indolyl, 1-methyl-5-benzimidazolyl, 1-methyl-6-benzimidazolyl, 1-ethyl-5-benzimidazolyl, 1-ethyl-6-benzimidazolyl, 3-, 4-, 5-, 6-, 7- or 8-hydroxy-2-quinolyl.

$R^1$ is preferably A, especially methyl, ethyl, propyl, isopropyl, butyl, isobutyl, or tert.-butyl, and also, preferably, cyclopropyl, cyclopentyl, cyclohexyl, phenyl, benzyl or morpholino.

$R^2$, $R^5$ and $R^6$ are preferably H or methyl, and also ethyl, propyl, isopropyl, butyl or isobutyl.

$R^3$ is preferably cyclohexylmethyl, and also, preferably, A, especially methyl, ethyl, propyl, isopropyl, butyl, isobutyl, sec.-butyl, pentyl, isopentyl (3-methylbutyl or 2-methylbutyl), phenyl, benzyl, p-chlorobenzyl, 2-chlorohexylethyl, bicyclo[2,2,1]heptyl-2-methyl or 6,6-dimethylbicyclo[3,1,1]heptyl-2-methyl.

$R^4$ is preferably (H, OH).

$R^7$ is preferably H, methyl, ethyl, isobutyl or sec.-butyl, and also, preferably, propyl, butyl, cyclohexylmethyl or benzyl.

$R^8$ is preferably H, methyl, ethyl, phenyl or 2-, 3- or 4-pyridyl.

$R^9$ and $R^{10}$ are preferably H, methyl, ethyl, phenyl or o-, m- or o-aminophenyl.

$R^{11}$ is preferably H, methyl or ethyl.

$R^{12}$ is preferably H, methyl, ethyl, phenyl or 2-, 3- or 4-pyridylmethyl $R^{13}$ is preferably H, methyl or ethyl.

L is preferably CH.

m, p and r are preferably 0, 1 or 2; n and s are preferably 1.

X is preferably H, POA, alkoxycarbonyl, such as ETOC, IPOC or BOC, CBZ, alkanoyl, such as acetyl, propionyl, butyryl or isobutyryl, cycloalkylcarbonyl, such as cyclopentylcarbonyl or cyclohexylcarbonyl, aroyl, such as benzoyl, arylalkanoyl, such as phenylacetyl, 2-phenylpropionyl, 3-phenylpropionyl, 4-phenylbutyryl, 2-benzyl-3-phenylpropionyl, PBB, 2-(2-phenylethyl)-4-phenylbutyryl, 2-(2-naphthylmethyl)-4-phenylbutyryl, 2-o-, -m- or p-fluorophenylpropionyl, 3-o-, -m- or -p-fluorophenylpropionyl, 2-o-, -m- or p-chlorophenylpropionyl, 3-o-, -m- or -p-chlorophenylpropionyl, cycloalkylalkanoyl, such as cyclohexylacetyl, 2-cyclohexylpropionyl or 3-cyclohexylpropionyl, or N-alkylcarbamoyl, such as ETNC or IPNC or MC. The radicals X which are particularly preferred are BOC and MC, and also ETOC, IPOC, ETNC, IPNC and PBB, and also H, POA, 4-phenylbutyryl, 2-benzyl-3-phenylpropionyl, 2-(2-phenylethyl)-4-phenylbutyryl, 2-(2-naphthylmethyl)-4-phenylbutyryl and CBZ.

Z is preferably 2, but also 0 or 1 and also 3 or 4, aminoacid radicals attached to one another by a peptide linkage, in particular one of the groups His, Phe-His, Pro-Phe-His or His-Pro-Phe-His, and also, preferably, the groups Abu, Ada, Asn, Bia, Cal, Gln, N-(im)-methyl-His, Leu, αNal, βNal, Nle, Phe, Trp, Tyr, Abu-His, Ada-His, Ala-His, Ala-Phe, Arg-His, Asn-His, Bia-His, Cal-His, Dab-His, Glu-His, His-His, Ile-His, Leu-His, tert.-Leu-His, Lys-His, Met-His, αNal-His, βNal-His, Nbg-His, Nle-His, (N-Me-His)-His, (N-Me-Phe)-His, Orn-His, Phe-Abu, Phe-Ada, Phe -Ala, Phe-Arg, Phe-Asn, Phe-Bia, Phe-Cal, Phe-Dab, Phe-Gln, Phe-Glu, Phe-(N-im-methyl-His), Phe-Ile, Phe-Leu, Phe-tert.-Leu, Phe-lys, Phe-Met, Phe-α-Nal, Phe-βNal, Phe-Nbg, Phe-Nle, Phe-(N-Me-His), Phe-(N-Me-Phe), Phe-Orn, Phe-Phe, Phe-Pro, Phe-Ser, Phe-Thr, Phe-Tic, Phe-Trp, Phe-Tyr, Phe-Val, Pro-His, Ser-His, Thr-His, Tic-His, Trp-His, Tyr-His, Val-His, and also, Ada-Phe-His, Pro-Ala-His, Pro-Ala-Phe, Pro-Phe-Ala, Pro-Phe-Phe, His-pro-Ala-His, His-Pro-Ala-Phe, His-Pro-Phe-Ala, His-Pro-Phe-Phe, and also Pro-Abu-His, Pro-Ada-His, Pro-Arg-His, Pro-Asn-His, Pro-Bia-His, Pro-Dab-His, Pro-Glu-His, Pro-His-His, Pro-Ile-His, Pro-Leu-His, Pro-tert.-Leu-His, Pro-Lys-His, Pro-Met-His, Pro-Nbg-His, Pro-Nle-His, Pro-(N-Me-His)-His, Pro-(N-Me-Phe)-His, Pro-Orn-His, Pro-Phe-Abu, Pro-Phe-Ada, Pro-Phe-Arg, Pro-Phe-Asn, Pro-Phe-Bia, Pro-Phe-Dab, Pro-Phe-Gln, Pro-Phe-Glu, Pro-Phe-(N-im-methyl-His), Pro-Phe-Ile, Pro-Phe-Leu, Pro-Phe-tert.-Leu, Pro-Phe-Lys, Pro-Phe-Met, Pro-Phe-Nbg, Pro-Phe-Nle, Pro-Phe-(N-Me-His), Pro-Phe-(N-Me-Phe), Pro-Phe-Orn, Pro-Phe-Pro, Pro-Phe-Ser, Pro-Phe-Thr, Pro-Phe-Tic, Pro-Phe-Trp, Pro-Phe-Tyr, Pro-Phe-Val, Pro-Pro-His, Pro-Ser-His, Pro-Thr-His, Pro-Tic-His, Pro-Trp-His, Pro-Tyr-His, Pro-Val-His, His-Pro-Abu-His, His-Pro-Ada-His, His-Pro-Arg-His, His-Pro-Asn-His, His-Pro-Bia-His, His-Pro-Dab-His, His-Pro-Glu-His, His-Pro-His-His, His-Pro-Ile-His, His-Pro-Leu-His, His-Pro-tert.-Leu-His, His-Pro-Lys-His, His-Pro-Met-His, His-Pro-Nbg-His, His-Pro-Nle-His, His-Pro-(N-Me-His)-His, His-Pro-(N-Me-Phe)-His, His-Pro-Orn-His, His-Pro-Phe-Abu, His-Pro-Phe-Ada, His-Pro-Phe-Arg, His-Pro-Phe-Asn, His-Pro-Phe-Bia, His-Pro-Phe-Dab, His-Pro-Phe-Gln, His-Pro-Phe-Glu, His-Pro-Phe-(N-im-methyl-His), His-Pro-Phe-Ile, His-Pro-Phe-Leu, His-Pro-Phe-tert.-Leu, His-Pro-Phe-Lys, His-Pro-Phe-Met, His-Pro-Phe-Nbg, His-Pro-Phe-Nle, His-Pro-Phe-(N-Me-His), His-pro-Phe-(N-Me-Phe), His-Pro-Phe-Orn, His-Pro-Phe-Pro, His-Pro-Phe-Ser, His-Pro-Phe-Thr, His-Pro-Phe-Tic, His-Pro-Phe-Trp, His-Pro-Phe-Tyr, His-Pro-Phe-Val, His-Pro-Pro-His, His-Pro-Ser-His, His-Pro-Thr-His, His-Pro-Tic-His, His-Pro-Trp-His, His-Pro-Tyr-His, His-Pro-Val-His E is preferably absent or is preferably Ile or Leu, and also, preferably, Abu, Cal, Met or Nle.

D is preferably 2-amino-4-thiazolyl, 2-($R^8$—CO—NH)-4-thiazolyl, 2-($R^9$—NH—CO—NH)-4-thiazolyl, 4-($R^{11}$OOC)-2-thiazolyl, 4-($R^{12}R^{13}$N—CO)-2-thiazolyl or 5-tetrazolyl.

The group W is preferably —NH—CHR$^3$—CHOH—CH$_2$—CO—, in particular —NH—CH(cyclohexylmethyl)—CHOH—CH$_2$—CO— ("AHCP", derived from 4-amino-3-hydroxy-5-cyclohexylpentanoic acid), and also —NH—CH(CH$_2$CH$_2$—cyclohexyl)—CHOH—CH$_2$—CO— ("AHCH"; derived from 4-amino-3-hydroxy-6-cyclohexylhexanoic acid), —NH—CH(isobutyl)—CHOH—CH$_2$—CO— ("Sta"; derived from statine) or —NH—CH(benzyl)—CHOH—CH$_2$—CO— ("AHPP"; derived from 4-amino-3-hydroxy-5-phenylpentanoic acid). The group W is preferably also —NH—CHR$^3$—CH(NH$_2$)—CH$_2$—CO—, in particular —NH—CH(cyclohexylmethyl)—CH(NH$_2$)—CH$_2$—CO— ("DACP"; derived from 3,4-diamino-5-cyclohexylpentanoic acid), —NH—CH(CH$_2$CH$_2$-cyclohexyl)—CH(NH$_2$)—CH$_2$—CO— ("DACH"; derived from 3,4-diamino-6-cyclohexylhexanoic acid), —NH—CH(isobutyl)—CH(NH$_2$)—CH$_2$—CO— ("DAMH"; derived from 3,4-diamino-6-methylheptanoic acid) or —NH—CH(benzyl)—CH(NH$_2$)—CH$_2$—CO— ("DAPP"; derived from 3,4-diamino-5-phenylpentanoic acid).

The group W contains at least one chiral center. The compounds of the formula I can, therefore, exist in different—optically inactive or optically active—forms. Formula I embraces all these forms. If W is —NH—CHR$^3$—CR$^4$—CH$_2$—CO— in which R$^4$=(H, OH) or (H, NH$_2$), the 3S-hydroxy-4S-amino enantiomers of 3S,4S-diamino enantiomers are preferred. In the designation of individual substances, unless anything to the contrary is indicated, the abbreviations AHCP, AHCH, Sta, AHPP, DACP, DACH, DAMH and DAPP relate in all cases to the 3S,4S-forms.

The abovementioned cycloalkyl, cycloalkylalkyl, Het, and phenyl groups, when substituted, preferably have 1–3, in particular 1 or 2, substitutents.

The above mentioned tetrazolyl, when substituted, and thiazolyl groups preferably have 1–2, in particular 1 substituent(s).

Accordingly, the invention relates in particular to compounds of the formula I in which at least one of the radicals mentioned has one of the preferred meanings indicated above. Some preferred groups of compounds can be expressed by means of the following partial formulae Ia to Ic which correspond to the formula I, but in which in Ia X is H, ETOC, IPOC, BOC, POA, CBZ, ETNC, IPNC, MC, 2-phenylbutyryl, 2-benzyl-3-phenylpropionyl, PBB, 2-(2-phenylethyl)-4-phenylbutyryl or 2-(2-naphthylmethyl)-4-phenylbutyryl, Z is absent or is His, Ada-His, Cal-His, αNal-His, βNal-His, Phe-Abu, Phe-Bia, Phe-Dab, Phe-His, Phe-N(im)-methyl-His, Phe-Leu, Phe-Lys, Phe-Met, Phe-Nle, or Phe-Orn, $R^2$ and $R^5$ are H, $R^3$ is isobutyl, cyclohexylmethyl, 2-cyclohexylethyl or benzyl, n and s are each 1, E is absent or is Ile or Leu, $R^7$ is H or alkyl having 1–4 C atoms and D is 2-amino-4-thiazolyl, 2-($R^8$—CO—NH)-4-thiazolyl, 2-($R^9$—NH—CO—NH)-4-thiazolyl, 4-($R^{11}$OOC)-2-thiazolyl, 4-($R^{12}$—$R^{13}$N—CO)-2-thiazolyl or 5-tetrazolyl;

in Ib

X is H, ETOC, IPOC, BOC, ETNC, IPNC, MC or PBB,

Z is His, Ada-His, Cal-His, α-Nal-His, β-Nal-His, Phe-Abu, Phe-Bia, Phe-Dab, Phe-His, Phe-N(im)-methyl-His, Phe-Leu, Phe-Lys, Phe-Met, Phe-Nle or Phe-Orn, $R^2$ and $R^5$ are H, $R^3$ is cyclohexylmethyl, $R^4$ is (H, OH), n and s are each 1, E is absent or is Ile or Leu, $R^7$ is H or alkyl having 1–4 C atoms, D is 2-amino-4-thiazolyl, 2-($R^8$—CO—NH)-4-thiazolyl, 2-($R^9$—NH—CO—NH)-4-thiazolyl, 4-($R^{11}$OOC)-2-thiazolyl, 4-($R^{12}R^{13}$N—CO)-2-thiazolyl or 5-tetrazolyl $R^8$ ia H, A, phenyl or pyridyl, $R^9$ is H, A, phenyl or aminophenyl, $R^{11}$ is A,
$R^{12}$ is H, A, phenyl or pyridylmethyl and
$R^{13}$ is H; and
in Ic
X is BOC, PBB or MC,
Z is His or Phe-His,
$R^2$ and $R^5$ are each H,
$R^3$ is cyclohexylmethyl,
$R^4$ is (H, OH),
n and s are each 1,
E is absent or is Ile or Leu,
$R^7$ is H, isobutyl or sec.-butyl and
D is 2-amino-4-thiazolyl, 2-N'-ethylureido-4-thiazolyl, 2-N'-m-aminophenylureido-4-thiazolyl, 4-ethoxycarbonyl-2-thiazolyl or 4-N'-(3-pyridylmethyl)-carbamoyl-2-thiazolyl.

Particularly preferred are compounds of formulae I', Ia', Ib' and Ic' which correspond to formula I, Ia, Ib and Ic, but wherein D is 5-tetrazolyl.

The compounds of the formula I and also the starting materials required for their preparation are, incidentally, prepared by methods which are in themselves known, such as are described in the literature (for example in the standard works such as Houben-Weyl, Methoden der organishen Chemie, ("Methods of organic chemistry"), Georg-Thieme-Verlag, Stuttgart; and also EP-A Nos. 45,665, 77,028, 77,029 or 81,783), specifically under reaction conditions which are known and suitable for the reactions mentioned. In this respect it is also possible to make use of variants which are in themselves known but are not mentioned here in detail.

If desired, the starting materials can also be formed in situ, so that they are not isolated from the reaction mixture, but are immediately reacted further to give the compounds of the formula I.

The compounds of the formula I are preferably obtained by setting them free from their functional derivatives by means of solvolysis, in particular hydrolysis, or by means of hydrogenolysis.

Preferred starting materials for the solvolysis or hydrogenolysis are those which, instead of one or more free amino and/or hydroxyl groups, contain corresponding protected amino and/or hydroxyl groups, preferably those which, instead of an H atom attached to an N atom, carry an amino protective group, for example those which correspond to the formula I, but, instead of an His group, contain an N(im)-$R^{14}$-His group (wherein $R^{14}$ is an amino protective group, for example BOM or DNP), or those of the formula X—Z—$NR^2$—$CHR^3$—CH($NHR^{14}$)—($CHR^5$)$_n$—CO—E—$NR^6$—($CHR^7$)$_s$—D.

Preferred starting materials are also those which, instead of the H atom of a hydroxyl group, carry a hydroxyl protective group, for example those of the formula X—Z—$NR^2$—$CHR^3$—$CHOR^{15}$—($CHR^5$)$_n$—CO—E—$NR^6$—($CHR^7$)$_s$—D, wherein $R^{15}$ is a hydroxyl protective group.

It is also possible for several—identical or different—protected amino and/or hydroxyl groups to be present in the molecule of the starting material. If the protective groups present are different from one another, they can in many cases be split off selectively.

The term "amino protective group" is generally known and related to groups which are suitable for protecting (blocking) an amino group against chemical reactions, but which can readily be removed after the desired chemical reaction at other points in the molecule has been carried out. In particular, unsubstituted or substituted acyl groups, aryl groups (for example DNP), aralkoxymethyl groups (for example BOM) or aralkyl groups (for example benzyl, 4-nitrobenzyl or triphenylmethyl) are typical of such groups. Since the amino protective groups are removed after the desired reaction (or reaction sequence), the nature and size are, after all, not critical; but those having 1-20, in particular 1-8, C atoms are preferred. The term "acyl group" in the context of the present process should be interpreted in the widest sense. It embraces acyl groups derived from aliphatic, araliphatic, aromatic or heterocyclic carboxylic acids or sulfonic acids and also, in particular, alkoxycarbonyl, aryloxycarbonyl and, above all, aralkoxycarbonyl groups. Examples of acyl groups of this type are alkanoyl, such as acetyl, propionyl or butyryl; aralkanoyl, such as phenylacetyl; aroyl, such as benzoyl or toluyl; aryloxyalkanoyl, such as POA; alkoxycarbonyl, such as methoxycarbonyl, ethoxycarbonyl, 2,2,2-trichloroethoxycarbonyl, BOC or 2-iodoethoxycarbonyl; or aralkyloxycarbonyl, such as CBZ ("carbobenzoxy"), 4-methoxybenyloxycarbonyl or FMOC. DNP and BOM, and also CBZ, FMOC, benzyl and acetyl, are preferred amino protective groups.

The term "hydroxyl protective group" is also generally known and relates to groups which are suitable for protecting a hydroxyl group against chemical reactions, but which can be removed readily after the desired chemical reaction at other points in the molecule has been carried out. The unsubstituted or substituted aryl, aralkyl or acyl groups mentioned above, and also alkyl groups, are typical of such groups. The nature and size of the hydroxyl protective groups are not critical, since they are removed again after the desired chemical reaction or reaction sequence; groups having 1-20, in particular 1-10, C atoms are preferred. Examples of hydroxyl protective groups are, inter alia: benzyl, p-nitrobenzoyl, p-toluenesulfonyl and acetyl, benzyl and acetyl being particularly preferred.

The functional derivatives of the compounds of the formula I to be used as starting materials can be prepared by customary methods of aminoacid and peptide synthesis, such as are described, for example, in the standard works and patent applications mentioned.

Depending on the protective group used, the compounds of the formula I are set free from their functional derivatives by means, for example, of strong acids, preferably trifluoroacetic acid or perchloric acid, but also other strong inorganic acids, such as hydrochloric acid or sulfuric acid, strong organic carboxylic acids, such as trichloroacetic acid, or sulfonic acids, such as benzensulfonic or p-toluenesulfonic acid. The presence of an additional inert solvent is possible, but not always necessary. Suitable inert solvents are preferably organic solvents, for example carboxylic acids, such as acetic acid, ethers, such as tetrahydrofuran or dioxane, amides, such as dimethylformamide (DMF), halogenated hydrocarbons, such as methylene dichloride, and also alcohols, such as methanol, ethanol or isopropanol, and also water. Mixtures of the abovementioned solvents are also suitable. Trifluoroacetic acid is preferably used in excess without the addition of a further solvent; perchloric acid is used in the form of a mixture of acetic acid and 70% perchloric acid in a 9:1 ratio. The reaction temperatures for the scission are preferably between about 0° and about 50°, it is preferable to carry out the reaction between 15° and 30° (room temperature).

The BOC group can, for example, be split off preferably by means of 40% trifluoroacetic acid in methylene chloride or by means of about 3 to 5N HCl in dioxane at 15°–30°; the FMOC group can be split off preferably by means of an approximately 5 to 20% solution of dimethylamine, diethylamine or piperidine in DMF at 15°–30°. The DNP group can also be split off, for example, by means of an approximately 3 to 10% solution of 2-mercaptoethanol in DMF/water at 15°–30°.

Protective groups which can be removed by hydrogenolysis (for example BOM, CBZ or benzyl) can be split off, for example, by treatment with hydrogen in the presence of a catalyst (for example a noble metal catalyst such as palladium, preferably on a support such as charcoal). Solvents suitable in this regard are those indicated above, in particular, for example, alcohols, such as methanol or ethanol, or amides, such as DMF. The hydrogenolysis is carried out as a rule at temperatures between about 0° and 100° and pressures between about 1 and 200 bar, preferably at 20°–30° and 1–10 bar. Hydrogenolyis of the CBZ group can, for example, be carried out readily over to 5 to 10% Pd-on-C in methanol at 20°–30°.

The compounds of the formula I can also be obtained by reducing corresponding compounds containing one or more additional C—C—and/or C—N—and/or C—O—bonds and/ or O atoms instead of H atoms. Thus, for example, amino compounds of the formula I containing a substituent Ar=aminophenyl, are obtained by reducing the corresponding nitro compounds, for example by catalytic hydrogenation under the conditions mentioned above for hydrogenolysis.

Compounds of the formula I can also be obtained by direct peptide synthesis from a carboxylic acid component (formula II) an an amine component (formula III). Examples of suitable carboxylic acid components are those of the partial formulae X—Z—OH, X—Z—W—OH or X—Z—W—E—OH, while examples of suitable amine components are those of the partial formulae H—W—E—NR$^6$—(CHR$^7$)$_s$—D, H—E—NR$^6$—(CHR$^7$)$_s$—D or H—NR$^6$—(CHR$^7$)$_s$—D. The peptide linkage can, however, also be attached within the group Z or E; in this reaction a carboxylic acid of the formula X—Z$^1$—OH or H—Z—W—E$^1$—OH is reacted with an amino compound of the formula H—Z$^2$—W—E—NR$^6$—(CHR$^7$)$_s$—D or H—E$^2$—NR$^6$—(CHR$^7$)$_s$—D wherein Z$^1$+Z$^2$=Z and E$^1$+E$^2$=E. These reactions are preferably carried out by customary methods of peptide synthesis, such as are described, for example in Houben-Weyl, l.c., volume 15/II, pages 1 to 806 (1974).

The reaction is preferably carried out in the presence of a dehydrating agent, for example a carbodiimide, such as DCCI or dimethylaminopropylethylcarbodiimide, and also propanephosphonic anhydride (cf. Angew Che. 92, 129 (1980)), diphenylphosphoryl azide or 2-ethoxy-N-ethoxycarbonyl-1,2-dihydroquinoline, in an inert solvent, for example a halogenated hydrocarbon, such as methylene dichloride, and ether, such as tetrahydrofuran or dioxane, and amide, such as DMF or dimethylacetamide, or a nitrile, such as acetonitrile, at temperatures between about −10 and 40, preferably between 0° and 30°.

Instead of II and III, it is also possible to employ in the reaction suitable reactive derivatives of these substances, for example derivatives in which reactive groups have been temporarily blocked by protective groups. The aminoacid derivatives III can, for example, be used in the form of their activated esters, which are preferably formed in situ, for example by adding HOBt or N-hydroxysuccinimide.

The starting materials of the formulae II and III are for the most part known. Insofar as they are not known, they can be prepared by known methods, for example the methods indicated above of peptide synthesis and the elimination of protective groups.

If desired, a functionally modified amino and/or hydroxyl group in a compound of the formula I can be liberated by solvolysis or hydrogenolysis in accordance with one of the methods described above.

Thus, in particular, a compound of the formula I wherein X is other than H can be converted into a compound of the formula I (X=H), preferably by hydrogenolysis, if X=CBZ, otherwise by selective solvolysis. If X=BOC, the BOC group can be eliminated, for example, by means of HCl in dioxane at room temperature.

It is also possible, for example, to reduce keto compounds of the formula I (R$^4$=O) to give compounds of the formula I (R$^4$=H, OH)), for example by means of a complex metal hydride, such as NaBH$_4$, which does not at the same time reduce the peptide carbonyl groups, in an inert solvent, such as methanol, at temperatures between about −10° and +30°.

Keto compounds of the formula I (R$^4$=O) can also be converted into compounds of the formula I (R$^4$=H, NH$_2$) by reductive amination. Reductive amination can be carried out in one or more stages. Thus it is possible, for example, to treat the keto compounds with ammonium salts, for example ammonium acetate, and NaCNBH$_3$, preferably in an inert solvent, for example an alcohol, such as methanol, at temperatures between about 0° and 50°, especially between 15° and 30°. It is also possible first to convert the keto compound into the oxim in a customary manner by means of hydroxylamine, and to reduce this oxime, for example by catalytic hydrogenation over raney nickel, to give the amine.

It is also possible to convert a radical D into another radical D by treatment with esterifying, solvolyzing or amidizing agents. Thus, an acid can be esterified, by means of an alcohol of the formula A—OH or a diazoalkane, for example diazomethane, or an ester can be saponified to give the corresponding acid, for example by means of aqueous dioxane sodium hydroxide solution at room temperature. It is also possible, for example, to convert an ester into the corresponding amide by treatment with ammonia or with an amine of the formula A—NH$_2$ or A$_2$NH.

A base of the formula I can be converted into the appropriate acid addition salt by means of an acid. Acids which afford physiologically acceptable salts are particularly suitable for this reaction. Thus it is possible to use inorganic acids, for example sulfuric acid, nitric acid, hydrogen halide acids, such as hydrochloric acid or hydrobromic acid, phosphoric acids such as orthophosphoric acid, or sulfamic acid, and also organic acids, in particular aliphatic, alicyclic, araliphatic, aromatic or heterocyclic, monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic or 3-phenylpropionic acid, citric acid, gluconic acid, ascorbic acid, nicotinic acid, isonicotinic acid, methanesulfonic or ethanesulfonic acid, ethanedisulfonic acid, 2- hydroxyethanesulfonic acid, benzenesulfonic acid, p-toluenesulfonic acid, naphthalenemonosulfonic and naphthalenedisulfonic acids or laurylsulfuric acid. Salts with physiologically unacceptable acids, for example picrates, can be used for isolating and/or purifying the compounds of the formula I.

The new compounds of the formula I and their physiologically acceptable salts can be used for the preparation of pharmaceutical formulations by bringing them into a suitable dosage form together with at least one excipient or auxiliary and, if desired, together with one or more further active compounds. The formulations thus obtained can be employed as medicaments in human or veterinary medicine. Suitable excipients are organic or inorganic substances which are suitable for enteral (for example oral or rectal) administration or parenteral administration or for administration in the form of an inhalation spray, and which do not react with the new compounds, for example water, vegetable oils, benzylalcohols, polyethylene glycols, glycerol triacetate and other fatty acid glycerides, gelatine, soya lecithin, carbohydrates, such as lactose or starch, magnesium stearate, talc or cellulose. Tablets, coated tablets, capsules, syrups, elixirs or drops are especially used for oral administration; lacquered tablets and capsules having coatings or capsule sheaths resistant to gastric juices are especially of interest. Suppositories are used for rectal administration; solutions, preferably oily or aqueous solutions, and also suspensions, emulsions or implants, are used for parenteral administration. Sprays containing the active compound either dissolved or suspended in a mixture of propellant gases (for example fluorochlorohydrocarbons) can be used for administration in the form of an inhalation spray. In this regard, it is preferable to use the active compound in a micronized form, it being possible for one or more additional physiologically acceptable solvents to be present, for example ethanol. Inhalation solutions can be administered by means of customary inhalers. The new compounds can also be lyophilized, and the resulting lyophilizates can be used, for example, for the preparation of injection formulations. The formulations indicated can be sterilized and/or can contain auxiliaries, such as preservatives, stabilizers and/or wetting agents, emulsifiers, salts for regulating the osmotic pressure, buffer substances, colorants and/or aroma substances. If desired, they can also contain one or more further active compounds, for example one or more vitamins.

As a rule, the substances according to the invention are administered analogously to other known, commercially available peptides, but especially analogously to the compounds described in EP-A No. 77,028, preferably in dosage between about 100 mg and 30 g, in particular between 500 mg and 5 g, per dosage unit. The daily dosage is preferably between about 2 and 600 mg/kg of body weight. The particular dose for each specific patient depends, however, on a very wide variety of factors, for example on the effectiveness of the particular compound employed, on the age, body weight, general state of health, sex, on the diet, on the time and route of administration, and on the rate of excretion, combination of medicaments and the severity of the particular disease to which the therapy applies. Parenteral administration is preferred.

Renin-dependent hypertension and hyperaldosteronism can be effectively treated by administration of doses between about 1 and 300, preferably 5 and 50 mg/kg of body weight for diagnostic purposes, the new amino acid derivatives can be administered in single doses between about 0.1 and 10 mg/kg of body weight.

In the following examples "customary working up" means as follows: If necessary, water is added, the mixture is neutralized and extracted with ether or methylene dichloride, the phases are separated, the organic phase is dried over sodium sulfate, filtered and evaporated and the product is purified by chromatography over silica gel and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

Example 1

The pH of a mixture of 932 mg of 2-amino-4-[1S-(3S-hydroxy-4S-(N-tert.-butoxycarbonyl-L-phenylalanyl-N(im)-(2,4-dinitrophenyl)-L-histidyl-amino)-5-cyclohexylpentanoylamino)-3-methylbutyl]-thiazole ["2-amino-4-(1S-BOC-Phe-imi-DNP-His-AHCP-amino-3-methylbutyl)-thiazole"]; obtainable by reacting 1-bromo-3S-BOC-amino-5-methylhexan-2-one with thiourea in methanol to give 2-amino-4-(1S-BOC-amino-3-methylbutyl)-thiazole (M.p. 142°–144°), splitting off the BOC group by means of 4N HCl in dioxane to give 2-amino-4-(1S-amino-3-methylbutyl)-thiazole, reacting the latter with BOC-AHCP-OH/DCCI/HOBt to give 2-amino-4-(1S-BOC-AHCP-amino-3-methylbutyl)-thiazole, splitting off the BOC group and subjecting the product to condensation with BOC-imi-DNP-His-OH to give 2-amino-4-(1S-BOC-imi-DNP-His-AHCP-amino-3-methylbutyl)-thiazole and again splitting off the BOC group and reacting the product with BOC-Phe-OH], 2 g of 2-mercaptoethanol, 20 ml of DMF and 20 ml of water is adjusted, with stirring, to pH 8 by means of aqueous $Na_2CO_3$ solution at 20°, and the mixture is stirred for 2 hours at 20°. Customary working up gives 2-amino-4-[1S-(3S-hydroxy-4S-(N-tert.-butoxycarbonyl-L-phenylalanyl-L-histidyl-amino)-5-cyclohexylpentanoylamino)-3-methylbutyl]-thiazole ["2-amino-4-(1S-BOC-Phe-His-AHCP-amino-3-methylbutyl)-thiazole"], M.p. 164°–166°.

The following are obtained analogously by subjecting the corresponding imi-DNP derivatives to scission:
2-amino-4-(1S-ETOC-Phe-His-AHCP-amino-2S-methybutyl)-thiazole
2-amino-4-(1S-IPOC-Phe-His-AHCP-amino-2S-methylbutyl)-thiazole
2-amino-4-(1S-BOC-Phe-His-AHCP-amino-2S-methylbutyl)-thiazole, M.p. 136°–138° [via 2-amino-4-(1S-BOC-amino-2S-methylbutyl)-thiazole (M.p. 144°–146°), 2-amino-4-(1S-BOC-AHCP-amino-2S-methylbutyl)-thiazole (M.p. 127°–129°),
2-amino-4-(1S-BOC-imi-DNP-His-AHCP-amino-2S-methylbutyl)-thiazole (M.p. 127°–129°) and 2-amino- 4-(1S-BOC-Phe-imi-DNP-His-AHCP-amino-2S-methylbutyl)-thiazole (M.p. 117°)]
2-amino-4-(1S-ETNC-Phe-His-AHCP-amino-2S-methylbutyl)-thiazole
2-amino-4-(1S-IPNC-Phe-His-AHCP-amino-2S-methylbutyl)-thiazole
2-amino-4-(1S-MC-Phe-His-AHCP-amino-2S-methylbutyl)-thiazole, M.p. 140°–141° (imi-DNP derivative, M.p. 130°–132°).

2-amino-4-(1S-ETOC-Phe-His-AHCP-amino-3-methylbutyl)-thiazole
2-amino-4-(1S-IPOC-Phe-His-AHCP-amino-3-methylbutyl)-thiazole
2-amino-4-(1S-ETNC-Phe-His-AHCP-amino-3-methylbutyl)-thiazole
2-amino-4-(1S-IPNC-Phe-His-AHCP-amino-3-methylbutyl)-thiazole
2-amino-4-(1S-MC-Phe-His-AHCP-amino-3-methylbutyl)-thiazole
2-amino-4-[1S-(3-oxo-4S-BOC-Phe-His-amino-5-cyclohexylpentanoylamino)-3-methylbutyl)-thiazole
2-amino-4-(1S-PBB-His-AHCP-amino-2S-methylbutyl)-thiazole
2-amino-4-(1S-PBB-His-AHCP-amino-3-methylbutyl)-thiazole, M.p. 117°–120°
2-amino-4-(ETOC-Phe-His-AHCP-Ile-aminomethyl)-thiazole
2-amino-4-(IPOC-Phe-His-AHCP-Ile-aminomethyl)-thiazole
2-amino-4-(BOC-Phe-His-AHCP-Ile-aminomethyl)-thiazole
2-amino-4-(ETNC-Phe-His-AHCP-Ile-aminomethyl)-thiazole
2-amino-4-(IPNC-Phe-His-AHCP-Ile-aminomethyl)-thiazole
2-amino-4-(MC-Phe-His-AHCP-Ile-aminomethyl)-thiazole 2-amino-4-(PBB-His-AHCP-Ile-aminomethyl)-thiazole
2-amino-4-(ETOC-Phe-His-AHCP-Leu-aminomethyl)-thiazole
2-amino-4-(IPOC-Phe-His-AHCP-Leu-aminomethyl)-thiazole
2-amino-4-(BOC-Phe-His-AHCP-Leu-aminomethyl)-thiazole
2-amino-4-(ETNC-Phe-His-AHCP-Leu-aminomethyl)-thiazole
2-amino-4-(IPNC-Phe-His-AHCP-Leu-aminomethyl)-thiazole
2-amino-4-(MC-Phe-His-AHCP-Leu-aminomethyl)-thiazole 2-ureido-4-(1S-ETOC-Phe-His-AHCP-amino-2S-methylbutyl)-thiazole
2-ureido-4-(1S-IPOC-Phe-His-AHCP-amino-2S-methylbutyl)-thiazole
2-ureido-4-(1S-BOC-Phe-His-AHCP-amino-2S-methylbutyl)-thiazole
2-ureido-4-(1S-ETNC-Phe-His-AHCP-amino-2S-methylbutyl)-thiazole
2-ureido-4-(1S-IPNC-Phe-His-AHCP-amino-2S-methylbutyl)-thiazole
2-ureido-4-(1S-MC-Phe-His-AHCP-amino-2S-methylbutyl)-thiazole M.p. 154° (dec.)
2-ureido-4-(1S-ETOC-Phe-His-AHCP-amino-3-methylbutyl)-thiazole
2-ureido-4-(1S-IPOC-Phe-His-AHCP-amino-3-methylbutyl)thiazole
2-ureido-4-(1S-BOC-Phe-His-AHCP-amino-3-methylbutyl)-thiazole
2-ureido-4-(1S-ETNC-Phe-His-AHCP-amino-3-methylbutyl)-thiazole
2-ureido-4-(1S-IPNC-Phe-His-AHCP-amino-3-methylbutyl)-thiazole
2-ureido-4-(1S-MC-Phe-His-AHCP-amino-3-methylbutyl)-thiazole
2-ureido-4-(1S-PBB-His-AHCP-amino-2S-methylbutyl)-thiazole
2-ureido-4-(1S-PBB-His-AHCP-amino-3-methylbutyl)-thiazole 2-ureido-4-(ETOC-Phe-His-AHCP-Ile-aminomethyl)-thiazole
2-ureido-4-(IPOC-Phe-His-AHCP-Ile-aminomethyl)-thiazole
2-ureido-4-(BOC-Phe-His-AHCP-Ile-aminomethyl)-thiazole
2-ureido-4-(ETNC-Phe-His-AHCP-Ile-aminoethyl)-thiazole
2-ureido-4-(IPNC-Phe-His-AHCP-Ile-aminomethyl)-thiazole
2-ureido-4-(MC-Phe-His-AHCP-Ile-aminomethyl)-thiazole 2-ureido-4-(PBB-His-AHCP-Ile-aminomethyl)-thiazole
2-ureido-4-(ETOC-Phe-His-AHCP-Leu-aminomethyl)-thiazole
2-ureido-4-(IPOC-Phe-His-AHCP-Leu-aminomethyl)-thiazole
2-ureido-4-(BOC-Phe-His-AHCP-Leu-aminomethyl)-thiazole
2-ureido-4-(ETNC-Phe-his-AHCP-Leu-aminomethyl)-thiazole
2-ureido-4-(IPNC-Phe-His-AHCP-Leu-aminomethyl)-thiazole
2-ureido-4-(MC-Phe-His-AHCP-Leu-aminomethyl)-thiazole 2-N'-methylureido-4-(1S-ETOC-Phe-His-AHCP-amino-2S-methylbutyl)-thiazole
2-N'-methylureido-4-(1S-IPOC-Phe-His-AHCP-amino-2S-methylbutyl)-thiazole
2-N'-methylureido-4-(1S-BOC-Phe-His-AHCP-amino-2S-methylbutyl)-thiazole
2-N'-methylureido-4-(1S-ETNC-Phe-His-AHCP-amino-2S-methylbutyl)-thiazole
2-N'-methylureido-4-(1S-IPNC-Phe-His-AHCP-amino-2S-methylbutyl)-thiazole
2-N'-methylureido-4-(1S-MC-Phe-His-AHCP-amino-2S-methylbutyl)-thiazole, M.p. 159° (dec.)

2-N'-methylureido-4-(1S-ETOC-Phe-His-AHCP-amino-3-methylbutyl)-thiazole
2-N'-methylureido-4-(1S-IPOC-Phe-His-AHCP-amino-3-methylbutyl)-thiazole
2-N'-methylureido-4-(1S-BOC-Phe-His-AHCP-amino-3-methylbutyl)-thiazole
2-N'-methylureido-4-(1S-ETNC-Phe-His-AHCP-amino-3-methylbutyl)-thiazole
2-N'-methylureido-4-(1S-IPNC-Phe-His-AHCP-amino-3-methylbutyl)-thiazole
2-N'-methylureido-4-(1S-MC-Phe-His-AHCP-amino-3-methylbutyl)-thiazole 2-N'-methylureido-4-(1S-PBB-His-AHCP-amino-2S-methylbutyl)-thiazole
2-N'-methylureido-4-(1S-PBB-His-AHCP-amino-3-methylbutyl)-thiazole 2-N'-methylureido-4-(ETOC-Phe-His-AHCP-Ile-aminomethyl)-thiazole
2-N'-methylureido-4-(IPOC-Phe-His-AHCP-Ile-aminomethyl)-thiazole
2-N'-methylureido-4-(BOC-Phe-His-AHCP-Ile-aminomethyl)-thiazole
2-N'-methylureido-4-(ETNC-Phe-His-AHCP-Ile-aminomethyl)-thiazole
2-N'-methylureido-4-(IPNC-Phe-His-AHCP-Ile-aminomethyl)-thiazole
2-N'-methylureido-4-(MC-Phe-His-AHCP-Ile-aminomethyl)-thiazole
2-N'-methylureido-4-(PBB-His-AHCP-Ile-aminomethyl)-thiazole
2-N'-methylureido-4-(ETOC-Phe-His-AHCP-Leu-aminomethyl)-thiazole
2-N'-methylureido-4-(IPOC-Phe-His-AHCP-Leu-aminomethyl)-thiazole
2-N'-methylureido-4-(BOC-Phe-His-AHCP-Leu-aminomethyl)-thiazole
2-N'-methylureido-4-(ETNC-Phe-His-AHCP-Leu-aminomethyl)-thiazole
2-N'-methylureido-4-(IPNC-Phe-His-AHCP-Leu-aminomethyl)-thiazole
2-N'-methylureido-4-(MC-Phe-His-AHCP-Leu-aminomethyl)-thiazole
2-N'-ethylureido-4-(1S-ETOC-Phe-His-AHCP-amino-2S-methylbutyl)-thiazole
2-N'-ethylureido-4-(1S-IPOC-Phe-His-AHCP-amino-2S-methylbutyl)-thiazole
2-N'-ethylureido-4-(1S-BOC-Phe-His-AHCP-amino-2S-methylbutyl)-thiazole, M.p. 134°–136° [via 2-amino-4-(1S-BOC-Phe-imi-DNP-His-AHCP-amino-2S-methylbutyl)-thiazole (M.p. 117°) and the reaction of the latter with ethyl isocyanate to give the 2-N'-ethylureido derivative (M.p. 135° decomposition)]
2-N'-ethylureido-4-(1S-ETNC-Phe-His-AHCP-amino-2S-methylbutyl)-thiazole
2-N'-ethylureido-4-(1S-IPNC-Phe-His-AHCP-amino-2S-methylbutyl)-thiazole
2-N'-ethylureido-4-(1S-MC-Phe-His-AHCP-amino-2S-methylbutyl)-thiazole 2-N'-ethylureido-4-(1S-ETOC-Phe-His-AHCP-amino-3-methylbutyl)-thiazole
2-N'-ethylureido-4-(1S-IPOC-Phe-His-AHCP-amino-3-methylbutyl)-thiazole
2-N'-ethylureido-4-(1S-BOC-Phe-His-AHCP-amino-3-methylbutyl)-thiazole
2-N'-ethylureido-4-(1S-ETNC-Phe-His-AHCP-amino-3-methylbutyl)-thiazole
2-N'-ethylureido-4-(1S-IPNC-Phe-His-AHCP-amino-3-methylbutyl)-thiazole
2-N'-ethylureido-4-(1S-MC-Phe-His-AHCP-amino-3-methylbutyl)-thiazole 2-N'-ethylureido-4-(1S-PBB-His-AHCP-amino-2S-methylbutyl)-thiazole
2-N'-ethylureido-4-(1S-PBB-His-AHCP-amino-3-methylbutyl)-thiazole 2-N'-ethylureido-4-(ETOC-Phe-His-AHCP-Ile-aminomethyl)-thiazole
2-N'-ethylureido-4-(IPOC-Phe-His-AHCP-Ile-aminomethyl)-thiazole
2-N'-ethylureido-4-(BOC-Phe-His-AHCP-Ile-aminomethyl)-thiazole
2-N'-ethylureido-4-(ETNC-Phe-His-AHCP-Ile-aminomethyl)-thiazole
2-N'-ethylureido-4-(IPNC-Phe-His-AHCP-Ile-aminomethyl)-thiazole
2-N'-ethylureido-4-(MC-Phe-His-AHCP-Ile-aminomethyl)-thiazole 2-N'-ethylureido-4-(PBB-His-AHCP-Ile-aminomethyl)-thiazole
2-N'-ethylureido-4-(ETOC-Phe-His-AHCP-Leu-aminomethyl)-thiazole
2-N'-ethylureido-4-(IPOC-Phe-His-AHCP-Leu-aminomethyl)-thiazole
2-N'-ethylureido-4-(BOC-Phe-His-ACHCP-Leu-aminomethyl)-thiazole
2-N'-ethylureido-4-(ETNC-Phe-His-AHCP-Leu-aminomethyl)-thiazole
2-N'-ethylureido-4-(IPNC-Phe-His-AHCP-Leu-aminomethyl)-thiazole
2-N'-ethylureido-4-(MC-Phe-His-AHCP-Leu-aminomethyl)-thiazole 2-N'-phenylureido-4-(1S-ETOC-Phe-His-AHCP-amino-2S-methylbutyl)-thiazole
2-N'-phenylureido-4-(1S-IPOC-Phe-His-AHCP-amino-2S-methylbutyl)-thiazole
2'-N'-phenylureido-4-(1S-BOC-Phe-His-AHCP-amino-2S-methylbutyl)-thiazole
2-N'-phenylureido-4-(1S-ETNC-Phe-His-AHCP-amino-2S-methylbutyl)-thiazole
2-N'-phenylureido-4-(1S-IPNC-Phe-His-AHCP-amino-2S-methylbutyl)-thiazole
2-N'-phenylureido-4-(1S-MC-Phe-His-AHCP-amino-2S-methylbutyl)-thiazole 2-N'-phenylureido-4-(1S-ETOC-Phe-His-AHCP-amino-3-methylbutyl)-thiazole
2-N'-phenylureido-4-(1S-IPOC-Phe-His-AHCP-amino-3-methylbutyl)-thiazole
2-N'-phenylureido-4-(1S-BOC-Phe-His-AHCP-amino-3-methylbutyl)-thiazole
2-N'-phenylureido-4-(1S-ETNC-Phe-His-AHCP-amino-3-methylbutyl)-thiazole
2-N'-phenylureido-4-(1S-IPNC-Phe-His-AHCP-amino-3-methylbutyl)-thiazole
2-N'-phenylureido-4-(1S-MC-Phe-His-AHCP-amino-3-methylbutyl)-thiazole
2-N'-phenylureido-4-(1S-PBB-His-AHCP-amino-2S-methylbutyl)-thiazole
2-N'-phenylureido-4-(1S-PBB-His-AHCP-amino-3-methylbutyl)-thiazole 2-N'-phenylureido-4-(ETOC-Phe-His-AHCP-Ile-aminomethyl)-thiazole
2-N'-phenylureido-4-(IPOC-Phe-His-AHCP-Ile-aminomethyl)-thiazole
2-N'-phenylureido-4-(BOC-Phe-His-AHCP-Ile-aminomethyl)-thiazole
2-N'-phenylureido-4-(ETNC-Phe-His-AHCP-Ile-aminomethyl)-thiazole
2-N'-phenylureido-4-(IPNC-Phe-His-AHCP-Ile-aminomethyl)-thiazole
2-N'-phenylureido-4-(MC-Phe-His-AHCP-Ile-aminomethyl)-thiazole 2-N'-phenylureido-4-(PBB-His-AHCP-Ile-aminomethyl)-thiazole
2-N'-phenylureido-4-(ETOC-Phe-His-AHCP-Leu-aminomethyl)-thiazole
2-N'-phenylureido-4-(IPOC-Phe-His-AHCP-Leu-aminomethyl)-thiazole
2-N'-phenylureido-4-(BOC-Phe-His-AHCP-Leu-aminomethyl)-thiazole
2-N'-phenylureido-4-(ETNC-Phe-His-AHCP-Leu-aminomethyl)-thiazole
2-N'-phenylureido-4-(IPNC-Phe-His-AHCP-Leu-aminomethyl)-thiazole
2-N'-phenylureido-4-(MC-Phe-His-AHCP-Leu-aminomethyl)-thiazole 2-formamido-4-(1S-ETOC-Phe-His-AHCP-amino-2S-methylbutyl)-thiazole
2-formamido-4-(1S-IPOC-Phe-His-AHCP-amino-2S-methylbutyl)-thiazole
2-formamido-4-(1S-BOC-Phe-His-AHCP-amino-2S-methylbutyl)-thiazole
2-formamido-4-(1S-ETNC-Phe-His-AHCP-amino-2S-methylbutyl)-thiazole
2-formamido-4-(1S-IPNC-Phe-His-AHCP-amino-2S-methylbutyl)-thiazole
2-formamido-4-(1S-MC-Phe-His-AHCP-amino-2S-methylbutyl)-thiazole 2-formamido-4-(1S-ETOC-Phe-His-AHCP-amino-3-methylbutyl)-thiazole
2-formamido-4-(1S-IPOC-Phe-His-AHCP-amino-3-methylbutyl)-thiazole
2-formamido-4-(1S-BOC-Phe-His-AHCP-amino-3-methylbutyl)-thiazole
2-formamido-4-(1S-ETNC-Phe-His-AHCP-amino-3-methylbutyl)-thiazole
2-formamido-4-(1S-IPNC-Phe-His-AHCP-amino-3-methylbutyl)-thiazole
2-formamido-4-(1S-MC-Phe-His-AHCP-amino-3-methylbutyl)-thiazole 2-formamido-4-(1S-PBB-His-AHCP-amino-2S-methylbutyl)-thiazole
2-formamido-4-(1S-PBB-His-AHCP-amino-3-methylbutyl)-thiazole
2-formamido-4-(ETOC-Phe-His-AHCP-Ile-aminomethyl)-thiazole
2-formamido-4-(IPOC-Phe-His-AHCP-Ile-aminomethyl)-thiazole
2-formamido-4-(BOC-Phe-His-AHCP-Ile-aminomethyl)-thiazole
2-formamido-4-(ETNC-Phe-His-AHCP-Ile-aminomethyl)-thiazole
2-formamido-4-(IPNC-Phe-His-AHCP-Ile-aminomethyl)-thiazole
2-formamido-4-(MC-Phe-His-AHCP-Ile-aminomethyl)-thiazole
2-formamido-4-(PBB-His-AHCP-Ile-aminomethyl)-thiazole
2-formamido-4-(ETOC-Phe-His-AHCP-Leu-aminomethyl)-thiazole
2-formamido-4-(IPOC-Phe-His-AHCP-Leu-aminomethyl)-thiazole
2-formamido-4-(BOC-Phe-His-AHCP-Leu-aminomethyl)-thiazole
2-formamido-4-(ETNC-Phe-His-AHCP-Leu-aminomethyl)-thiazole
2-formamido-4-(IPNC-Phe-His-AHCP-Leu-aminomethyl)-thiazole
2-formamido-4-(MC-Phe-His-AHCP-Leu-aminomethyl)-thiazole 2-acetamido-4-(1S-ETOC-Phe-His-AHCP-amino-2S-methylbutyl)-thiazole
2-acetamido-4-(1S-IPOC-Phe-His-AHCP-amino-2S-methylbutyl)-thiazole
2-acetamido-4-(1S-BOC-Phe-His-AHCP-amino-2S-methylbutyl)-thiazole
2-acetamido-4-(1S-ETNC-Phe-His-AHCP-amino-2S-methylbutyl)-thiazole
2-acetamido-4-(1S-IPNC-Phe-His-AHCP-amino-2S-methylbutyl)-thiazole
2-acetamido-4-(1S-MC-Phe-His-AHCP-amino-2S-methylbutyl)-thiazole
2-acetamido-4-(1S-ETOC-Phe-His-AHCP-amino-3-methylbutyl)-thiazole
2-acetamido-4-(1S-IPOC-Phe-His-AHCP-amino-3-methylbutyl)-thiazole
2-acetamido-4-(1S-BOC-Phe-His-AHCP-amino-3-methylbutyl)-thiazole
2-acetamido-4-(1S-ETNC-Phe-His-AHCP-amino-3-methylbutyl)-thiazole
2-acetamido-4-(1S-IPNC-Phe-His-AHCP-amino-3-methylbutyl)-thiazole
2-acetamido-4-(1S-MC-Phe-His-AHCP-amino-3-methylbutyl)-thiazole
2-acetamido-4-(1S-PBB-His-AHCP-amino-2S-methylbutyl)-thiazole
2-acetamido-4-(1S-PBB-His-AHCP-amino-3-methylbutyl)-thiazole 2-acetamido-4-(ETOC-Phe-His-AHCP-Ile-aminomethyl)-thiazole
2-acetamido-4-(IPOC-Phe-His-AHCP-Ile-aminomethyl)-thiazole
2-acetamido-4-(BOC-Phe-His-AHCP-Ile-aminomethyl)-thiazole
2-acetamido-4-(ETNC-Phe-His-AHCP-Ile-aminomethyl)-thiazole
2-acetamido-4-(IPNC-Phe-His-AHCP-Ile-aminomethyl)-thiazole
2-acetamido-4-(MC-Phe-His-AHCP-Ile-aminomethyl)-thiazole
2-acetamido-4-(PBB-His-AHCP-Ile-aminomethyl)-thiazole
2-acetamido-4-(ETOC-Phe-His-AHCP-Leu-aminomethyl)-thiazole
2-acetamido-4-(IPOC-Phe-His-AHCP-Leu-aminomethyl)-thiazole
2-acetamido-4-(BOC-Phe-His-AHCP-Leu-aminomethyl)-thiazole
2-acetamido-4-(ETNC-Phe-His-AHCP-Leu-aminomethyl)-thiazole
2-acetamido-4-(IPNC-Phe-His-AHCP-Leu-aminomethyl)-thiazole
2-acetamido-4-(MC-Phe-His-AHCP-Leu-aminomethyl)-thiazole 2-benzamido-4-(1S-ETOC-Phe-His-AHCP-amino-2S-methylbutyl)-thiazole
2-benzamido-4-(1S-IPOC-Phe-His-AHCP-amino-2S-methylbutyl)-thiazole 2-benzamido-4-(1S-BOC-Phe-His-AHCP-amino-2S-methylbutyl)-thiazole
2-benzamido-4-(1S-ETNC-Phe-His-AHCP-amino-2S-methylbutyl)-thiazole
2-benzamido-4-(1S-IPNC-Phe-His-AHCP-amino-2S-methylbutyl)-thiazole
2-benzamido-4-(1S-MC-Phe-His-AHCP-amino-2S-methylbutyl)-thiazole 2-benzamido-4-(1S-ETOC-Phe-His-AHCP-amino-3-methylbutyl)-thiazole
2-benzamido-4-(1S-IPOC-Phe-His-AHCP-amino-3-methylbutyl)-thiazole
2-benzamido-4-(1S-BOC-Phe-His-AHCP-amino-3-methylbutyl)-thiazole
2-benzamido-4-(1S-ETNC-Phe-His-AHCP-amino-3-methylbutyl)-thiazole
2-benzamido-4-(1S-IPNC-Phe-His-AHCP-amino-3-methylbutyl)-thiazole
2-benzamido-4-(1S-MC-Phe-His-AHCP-amino-3-methylbutyl)-thiazole 2-benzamido-4-(1S-PBB-His-AHCP-amino-2S-methylbutyl)-thiazole
2-benzamido-4-(1S-PBB-His-AHCP-amino-3-methylbutyl)-thiazole 2-benzamido-4-(ETOC-Phe-His-AHCP-Ile-aminomethyl)-thiazole
2-benzamido-4-(IPOC-Phe-His-AHCP-Ile-aminomethyl)-thiazole
2-benzamido-4-(BOC-Phe-His-AHCP-Ile-aminomethyl)-thiazole
2-benzamido-4-(ETNC-Phe-His-AHCP-Ile-aminomethyl)-thiazole
2-benzamido-4-(IPNC-Phe-His-AHCP-Ile-aminomethyl)-thiazole
2-benzamido-4-(MC-Phe-His-AHCP-Ile-aminomethyl)-thiazole 2-benzamido-4-(PBB-His-AHCP-Ile-aminomethyl)-thiazole
2-benzamido-4-(ETOC-Phe-His-AHCP-Leu-aminomethyl)-thiazole
2-benzamido-4-(IPOC-Phe-His-AHCP-Leu-aminomethyl)-thiazole
2-benzamido-4-(BOC-Phe-His-AHCP-Leu-aminomethyl)-thiazole
2-benzamido-4-(ETNC-Phe-His-AHCP-Leu-aminomethyl)-thiazole
2-benzamido-4-(IPNC-Phe-His-AHCP-Leu-aminomethyl)-thiazole
2-benzamido-4-(MC-Phe-His-AHCP-Leu-aminomethyl)-thiazole 2-picolinamido-4-(1S-ETOC-Phe-His-AHCP-amino-2S-methylbutyl)-thiazole
2-picolinamido-4-(1S-IPOC-Phe-His-AHCP-amino-2S-methylbutyl)-thiazole
2-picolinamido-4-(1S-BOC-Phe-His-AHCP-amino-2S-methylbutyl)-thiazole
2-picolinamido-4-(1S-ETNC-Phe-His-AHCP-amino-2S-methylbutyl)-thiazole
2-picolinamido-4-(1S-IPNC-Phe-His-AHCP-amino-2S-methylbutyl)-thiazole
2-picolinamido-4-(1S-MC-Phe-His-AHCP-amino-2S-methylbutyl)-thiazole 2-picolinamido-4-(1S-ETOC-Phe-His-AHCP-amino-3-methylbutyl)-thiazole
2-picolinamido-4-(1S-IPOC-Phe-His-AHCP-amino-3-methylbutyl)-thiazole
2-picolinamido-4-(1S-BOC-Phe-His-AHCP-amino-3-methylbutyl)-thiazole
2-picolinamido-4-(1S-ETNC-Phe-His-AHCP-amino-3-methylbutyl)-thiazole
2-picolinamido-4-(1S-IPNC-Phe-His-AHCP-amino-3-methylbutyl)-thiazole
2-picolinamido-4-(1S-MC-Phe-His-AHCP-amino-3-methylbutyl)-thiazole 2-picolinamido-4-(1S-PBB-His-AHCP-amino-2S-methylbutyl)-thiazole
2-picolinamido-4-(1S-PBB-His-AHCP-amino-3-methylbutyl)-thiazole
2-picolinamido-4-(ETOC-Phe-His-AHCP-Ile-aminomethyl)-thiazole
2-picolinamido-4-(IPOC-Phe-His-AHCP-Ile-aminomethyl)-thiazole
2-picolinamido-4-(BOC-Phe-His-AHCP-Ile-aminomethyl)-thiazole
2-picolinamido-4-(ETNC-Phe-His-AHCP-Ile-aminomethyl)-thiazole
2-picolinamido-4-(IPNC-Phe-His-AHCP-Ile-aminomethyl)-thiazole
2-picolinamido-4-(MC-Phe-His-AHCP-Ile-aminomethyl)-thiazole 2-picolinamido-4-(PBB-His-AHCP-Ile-aminomethyl)-thiazole
2-picolinamido-4-(ETOC-Phe-His-AHCP-Leu-aminomethyl)-thiazole
2-picolinamido-4-IPOC-Phe-His-AHCP-Leu-aminomethyl)-thiazole
2-picolinamido-4-(BOC-Phe-His-AHCP-Leu-aminomethyl)-thiazole
2-picolinamido-4-(ETNC-Phe-His-AHCP-Leu-aminomethyl)-thiazole
2-picolinamido-4-(IPNC-Phe-His-AHCP-Leu-aminomethyl)-thiazole
2-picolinamido-4-(MC-Phe-His-AHCP-Leu-aminomethyl)-thiazole 2-(1S-ETOC-Phe-His-AHCP-amino-2S-methylbutyl)-4-ethoxycarbonylthiazole
2-(1S-IPOC-Phe-His-AHCP-amino-2S-methylbutyl)-4-ethoxycarbonylthiazole
2-(1S-BOC-Phe-His-AHCP-amino-2S-methylbutyl)-4-ethoxycarbonylthiazole, M.p. 115°–117°
2-(1S-ETNC-Phe-His-AHCP-amino-2S-methylbutyl)-4-ethoxycarbonylthiazole
2-(1S-IPNC-Phe-His-AHCP-amino-2S-methylbutyl)-4-ethoxycarbonylthiazole
2-(1S-MC-Phe-His-AHCP-amino-2S-methylbutyl)-4-ethoxycarbonylthiazole, M.p. 120°–122°
2-(1S-ETOC-Phe-His-AHCP-amino-3-methylbutyl)-4-ethoxycarbonylthiazole
2-(1S-IPOC-Phe-His-AHCP-amino-3-methylbutyl)-4-ethoxycarbonylthiazole
2-(1S-BOC-Phe-His-AHCP-amino-3-methylbutyl)-4-ethoxycarbonylthiazole
2-(1S-ETNC-Phe-His-AHCP-amino-3-methylbutyl)-4-ethoxycarbonylthiazole
2-(1S-IPNC-Phe-His-AHCP-amino-3-methylbutyl)-4-ethoxycarbonylthiazole 2-(1S-MC-Phe-His-AHCP-amino-3-methylbutyl)-4-ethoxycarbonylthiazole
2-(1S-PBB-His-AHCP-amino-2S-methylbutyl)-4-ethoxycarbonylthiazole
2-(1S-PBB-His-AHCP-amino-3-methylbutyl)-4-ethoxycarbonylthiazole 2-(ETOC-Phe-His-AHCP-Ile-aminomethyl)-4-ethoxycarbonylthiazole
2-(IPOC-Phe-His-AHCP-Ile-aminomethyl)-4-ethoxycarbonylthiazole
2-(BOC-Phe-His-AHCP-Ile-aminomethyl)-4-ethoxycarbonylthiazole
2-(ETNC-Phe-His-AHCP-Ile-aminomethyl)-4-ethoxycarbonylthiazole
2-(IPNC-Phe-His-AHCP-Ile-aminomethyl)-4-ethoxycarbonylthiazole
2-(MC-Phe-HIs-AHCP-Ile-aminomethyl)-4-ethoxycarbonylthiazole
2-(PBB-His-AHCP-Ile-aminomethyl)-4-ethoxycarbonylthiazole
2-(ETOC-Phe-His-AHCP-Leu-aminomethyl)-4-ethoxycarbonylthiazole
2-(IPOC-Phe-His-AHCP-Leu-aminomethyl)-4-ethoxycarbonylthiazole
2-(BOC-Phe-His-AHCP-Leu-aminomethyl)-4-ethoxycarbonylthiazole
2-(ETNC-Phe-His-AHCP-Leu-aminomethyl)-4-ethoxycarbonylthiazole
2-(IPNC-Phe-His-AHCP-Leu-aminomethyl)-4-ethoxycarbonylthiazole
2-(MC-Phe-His-AHCP-Leu-aminomethyl)-4-ethoxycarbonylthiazole 2-(1S-ETOC-Phe-His-AHCP-amino-2S-methylbutyl)-4-carbamoylthiazole
2-(1S-IPOC-Phe-His-AHCP-amino-2S-methylbutyl)-4-carbamoylthiazole
2-(1S-BOC-Phe-His-AHCP-amino-2S-methylbutyl)-4-carbamoylthiazole
2-(1s-ETNC-Phe-His-AHCP-amino-2S-methylbutyl)-4-carbamoylthiazole
2-(1S-IPNC-Phe-His-AHCP-amino-2S-methylbutyl)-4-carbamoylthiazole
2-(1S-MC-Phe-His-AHCP-amino-2S-methylbutyl)-4-carbamoylthiazole 2-(1S-ETOC-Phe-His-AHCP-amino-3-methylbutyl)-4-carbamoylthiazole
2-(1S-IPOC-Phe-His-AHCP-amino-3-methylbutyl)-4-carbamoylthiazole
2-(1S-BOC-Phe-His-AHCP-amino-3-methylbutyl)-4-carbamoylthiazole
2-(1S-ETNC-Phe-His-AHCP-amino-3-methylbutyl)-4-carbamoylthiazole
2-(1S-IPNC-Phe-His-AHCP-amino-3-methylbutyl)-4-carbamoylthiazole
2-(1S-MC-Phe-His-AHCP-amino-3-methylbutyl)-4-carbamoylthiazole 2-(1S-PBB-His-AHCP-amino-2S-methylbutyl)-4-carbamoylthiazole
2-(1S-PBB-His-AHCP-amino-3-methylbutyl)-4-carbamoylthiazole 2-(ETOC-Phe-His-AHCP-Ile-aminomethyl)-4-carbamoylthiazole
2-(IPOC-Phe-His-AHCP-Ile-aminomethyl)-4-carbamoylthiazole
2-(BOC-Phe-His-AHCP-Ile-aminomethyl)-4-carbamoylthiazole
2-(ETNC-Phe-His-AHCP-Ile-aminomethyl)-4-carbamoylthiazole
2-(IPNC-Phe-His-AHCP-Ile-aminomethyl)-4-carbamoylthiazole
2-(MC-Phe-His-AHCP-Ile-aminomethyl)-4-carbamoylthiazole 2-(PBB-His-AHCP-Ile-aminomethyl)-4-carbamoylthiazole
2-(ETOC-Phe-His-AHCP-Leu-aminomethyl)-4-carbamoylthiazole
2-(IPOC-Phe-His-AHCP-Leu-aminomethyl)-4-carbamoylthiazole
2-(BOC-Phe-His-AHCP-Leu-aminomethyl)-4-carbamoylthiazole
2-(ETNC-Phe-His-AHCP-Leu-aminomethyl)-4-carbamoylthiazole
2-(IPNC-Phe-His-AHCP-Leu-aminomethyl)-4-carbamoylthiazole
2-(MC-Phe-His-AHCP-Leu-aminomethyl)-4-carbamoylthiazole 2-(1S-ETOC-Phe-His-AHCP-amino-2S-methylbutyl)-4-N-methylcarbamoylthiazole
2-(1S-IPOC-Phe-His-AHCP-amino-2S-methylbutyl)-4-N-methylcarbamoylthiazole
2-(1S-BOC-Phe-His-AHCP-amino-2S-methylbutyl)-4-N-methylcarbamoylthiazole
2(1S-ETNC-Phe-His-AHCP-amino-2S-methylbutyl)-4-N-methylcarbamoylthiazole
2(1S-IPNC-Phe-His-AHCP-amino-2S-methylbutyl)-4-N-methylcarbamoylthiazole
2-(1S-MC-Phe-His-AHCP-amino-2S-methylbutyl)-4-N-methylcarbamoylthiazole 2-(1S-ETOC-Phe-His-AHCP-amino-3-methylbutyl)-4-N-methylcarbamoylthiazole
2-(1S-IPOC-Phe-His-AHCP-amino-3-methylbutyl)-4-N-methylcarbamoylthiazole
2-(1S-BOC-Phe-His-AHCP-amino-3-methylbutyl)-4-N-methylcarbamoylthiazole
2-(1S-ETNC-Phe-His-AHCP-amino-3-methylbutyl)-4-N-methylcarbamoylthiazole
2-(1S-IPNC-Phe-His-AHCP-amino-3-methylbutyl)-4-N-methylcarbamoylthiazole
2-(1S-MC-Phe-His-AHCP-amino-3-methylbutyl)-4-N-methylcarbamoylthiazole 2-(1S-PBB-His-AHCP-amino-2S-methylbutyl)-4-N-methylcarbamoylthiazole
2-(1S-PBB-His-AHCP-amino-3-methylbutyl)-4-N-methylcarbamoylthiazole 2-(ETOC-Phe-His-AHCP-Ile-aminomethyl)-4-N-methylcarbamoylthiazole
2-(IPOC-Phe-His-AHCP-Ile-aminomethyl)-4-N-methylcarbamoylthiazole
2-(BOC-Phe-His-AHCP-Ile-aminomethyl)-4-N-methylcarbamoylthiazole
1-(ETNC-Phe-His-AHCP-Ile-aminomethyl)-4-N-methylcarbamoylthiazole
2-(IPNC-Phe-His-AHCP-Ile-aminomethyl)-4-N-methylcarbamoylthiazole 2-(MC-Phe-His-AHCP-Ile-aminomethyl)-4-methylcarbamoylthiazole
2-(PBB-His-AHCP-Ile-aminomethyl)-4-N-methylcarbamoylthiazole
2-(ETOC-Phe-His-AHCP-Leu-aminomethyl)-4-N-methylcarbamoylthiazole
2-(IPOC-Phe-His-AHCP-Leu-aminomethyl)-4-N-methylcarbamoylthiazole
2-(BOC-Phe-His-AHCP-Leu-aminomethyl)-4-N-methylcarbamoylthiazole
2-(ETNC-Phe-His-AHCP-Leu-aminomethyl)-4-N-methylcarbamoylthiazole
2-(IPNC-Phe-His-AHCP-Leu-aminomethyl)-4-N-methylcarbamoylthiazole
2-(MC-Phe-His-AHCP-Leu-aaminomethyl)-4-N-methylcarbamoylthiazole 2-(1S-ETOC-Phe-His-AHCP-amino-2S-methylbutyl)-4-N-phenylcarbamoylthiazole
2-(1S-IPOC-Phe-Hos-AHCP-amino-2S-methylbutyl)-4-N-phenylcarbamoylthiazole
2-(1S-BOC-Phe-His-AHCP-amino-2S-methylbutyl)-4-N-phenylcarbamoylthiazole
2-(1S-ETNC-Phe-His-AHCP-amino-2S-methylbutyl)-4-N-phenylcarbamoylthiazole
2-(1S-IPNC-Phe-His-AHCP-amino-2S-methylbutyl)-4-N-phenylcarbamoylthiazole
2-(1S-MC-Phe-His-AHCP-amino-2S-methylbutyl)-4-N-phenylcarbamoylthiazole 2-(1S-ETOC-Phe-His-AHCP-amino-3-methylbutyl)-4-N-phenylcarbamoylthiazole
2-(1S-IPOC-Phe-His-AHCP-amino-3-methylbutyl)-4-N-phenylcarbamoylthiazole
2-(1S-BOC-Phe-His-AHCP-amino-3-methylbutyl)-4-N-phenylcarbamoylthiazole
2-(1S-ETNC-Phe-His-AHCP-amino-3-methylbutyl)-4-N-phenylcarbamoylthiazole
2-(1S-IPNC-Phe-His-AHCP-amino-3-methylbutyl)-4-N-phenylcarbamoylthiazole
2-(1S-MC-Phe-His-AHCP-amino-3-methylbutyl)-4-N-phenylcarbamoylthiazole 2-(1S-PBB-His-AHCP-amino-2S-methylbutyl)-4-N-phenylcarbamoylthiazole
2-(1S-PBB-His-AHCP-amino-3-methylbutyl)-4-N-phenylcarbamoylthiazole
2-(ETOC-Phe-His-AHCP-Ile-aminomethyl)-4-N-phenylcarbamoylthiazole
2-(IPOC-Phe-His-AHCP-Ile-aminomethyl)-4-N-phenylcarbamoylthiazole
2-(BOC-Phe-His-AHCP-Ile-aminomethyl)-4-N-phenylcarbamoylthiazole
2-(ETNC-Phe-His-AHCP-Ile-aminomethyl)-4-N-phenylcarbamoylthiazole
2-(IPNC-Phe-His-AHCP-Ile-aminomethyl)-4-N-phenylcarbamoylthiazole
2-(MC-Phe-His-AHCP-Ile-aminomethyl)-4-phenylcarbamoylthiazole 2-(PBB-His-AHCP-Ile-aminomethyl)-4-N-phenylcarbamoylthiazole
2-(ETOC-Phe-His-AHCP-Leu-aminomethyl)-4-N-phenylcarbamoylthiazole
2-(IPOC-Phe-His-AHCP-Leu-aminomethyl)-4-N-phenylcarbamoylthiazole
2-(BOC-Phe-His-AHCP-Leu-aminomethyl)-4-N-phenylcarbamoylthiazole
2-(ETNC-Phe-His-AHCP-Leu-aminomethyl)-4-N-phenylcarbamoylthiazole
2-(IPNC-Phe-His-AHCP-Leu-aminomethyl)-4-N-phenylcarbamoylthiazole
2-(MC-Phe-His-AHCP-Leu-aminomethyl)-4-N-phenylcarbamoylthiazole 2-(1S-ETOC-Phe-His-AHCP-amino-2S-methylbutyl)-4-N-(3-pyridylmethyl)-carbamoylthiazole
2-(1S-IPOC-Phe-His-AHCP-amino-2S-methylbutyl)-4-N-(3-pyridylmethyl)-carbamoylthiazole
2-(1S-BOC-Phe-His-AHCP-amino-2S-methylbutyl)-4-N-(3-pyridylmethyl)-carbamoylthiazole
2-(1S-ETNC-Phe-His-AHCP-amino-2S-methylbutyl)-4-N-(3-pyridylmethyl)-carbamoylthiazole
2-(1S-IPNC-Phe-His-AHCP-amino-2S-methylbutyl)-4-N-(;b 3-pyridylmethyl)-carbamoylthiazole
2-(1S-MC-Phe-His-AHCP-amino-2S-methylbutyl)-4-N-(3-pyridylmethyl)-carbamoylthiazole 2-(1S-ETOC-Phe-His-AHCP-amino-3-methylbutyl)-4-N-(3-pyridylmethyl)-carbamoylthiazole
2-(1S-IPOC-Phe-His-AHCP-amino-3-methylbutyl)-4-N-(3-pyridylmethyl)-carbamoylthiazole
2-(1S-BOC-Phe-His-AHCP-amino-3-methylbutyl)-4-N-(3-pyridylmethyl)-carbamoylthiazole, M.p. 137°–140° [obtained from ethyl 2-(1S-BOC-amino-3-methylbutyl)-thiazole-4-carboxylate via the free acid (M.p. 66°–68°), 2-(1S-BOC-amino-3-methylbutyl)-4-N-(3-pyridylmethyl)-carbamoylthiazole (M.p. 63°–65°), 2-(1S-BOC-AHCP-amino-3-methylbutyl)-4-N-(3-pyridylmethyl)-carbamoylthiazole (M.p. 92°–94°) and 2-(1S-BOC-phe-imi-DNP-His-AHCP-amino-3-methylbutyl)-4-N-(3-pyridylmethyl)-carbamoylthiazole (M.p. 160°, decomposition)]
2-(1S-ETNC-Phe-His-AHCP-amino-3-methylbutyl)-4-N-(3-pyridylmethyl)-carbamoylthiazole
2-(1S-IPNC-Phe-His-AHCP-amino-3-methylbutyl)-4-N-(3-pyridylmethyl)-carbamoylthiazole
2-(1S-MC-Phe-His-AHCP-amino-3-methylbutyl)-4-N-(3-pyridylmethyl)-carbamoylthiazole
2-(1S-PBB-His-AHCP-amino-2S-methylbutyl)-4-N-(3-pyridylmethyl)-carbamoylthiazole
2-(1S-PBB-His-AHCP-amino-3-methylbutyl)-4-N-(3-pyridylmethyl)-carbamoylthiazole 2-(ETOC-Phe-His-AHCP-Ile-aminomethyl)-4-N-(3-pyridylmethyl)-carbamoylthiazole
2-(IPOC-Phe-His-AHCP-Ile-aminomethyl)-4-(3-pyridylmethyl)-carbamoylthiazole
2-(BOC-Phe-His-AHCP-Ile-aminomethyl)-4-N-(3-pyridylmethyl)-carbamoylthiazole
2-(ETNC-Phe-His-AHCP-Ile-aminomethyl)-4-N-(3-pyridylmethyl)-carbamoylthiazole
2-(IPNC-Phe-His-AHCP-Ile-aminomethyl)-4-N-(3-pyridylmethyl)-carbamoylthiazole
2-(MC-Phe-His-AHCP-Ile-aminomethyl)-4-(3-pyridylmethyl)-carbamoylthiazole 2-(PBB-His-AHCP-Ile-aminomethyl)-4-N-(3-pyridylmethyl)-carbamoylthiazole
2-(ETOC-Phe-His-AHCP-Leu-aminomethyl)-4-N-(3-pyridylmethyl)-carbamoylthiazole
2-(IPOC-Phe-His-AHCP-Leu-aminomethyl)-4-N-(3-pyridylmethyl)-carbamoylthiazole
2-(BOC-Phe-His-AHCP-Leu-aminomethyl)-4-N-(3-pyridylmethyl)-carbamoylthiazole 2-(ETNC-Phe-His-AHCP-Leu-aminomethyl)-4-N-(3-pyridylmethyl)-carbamoylthiazole
2-(IPNC-Phe-His-AHCP-Leu-aminomethyl)-4-N-(3-pyridylmethyl)-carbamoylthiazole
2-(MC-Phe-His-AHCP-Leu-aminomethyl)-4-N-(3-pyridylmethyl)-carbamoylthiazole 5-(MC-Phe-His-AHCP-aminomethyl)-tetrazole
5-(1S-ETOC-Phe-His-AHCP-amino-2S-methylbutyl)-tetrazole
5-(1S-IPOC-Phe-His-AHCP-amino-2S-methylbutyl)-tetrazole
5-(1S-BOC-Phe-His-AHCP-amino-2S-methylbutyl)-tetrazole, M.P. 117°
5-(1S-ETNC-Phe-His-AHCP-amino-2S-methylbutyl)-tetrazole
5-(1S-IPNC-Phe-His-AHCP-amino-2S-methylbutyl)-tetrazole
5-(1S-MC-Phe-His-AHCP-amino-2S-methylbutyl)-tetrazole 5-(1S-ETOC-Phe-His-AHCP-amino-3-methylbutyl)-tetrazole
5-(1S-IPOC-Phe-His-AHCP-amino-3-methylbutyl)-tetrazole
5-(1S-BOC-Phe-His-AHCP-amino-3-methylbutyl)-tetrazole
5-(1S-ETNC-Phe-His-AHCP-amino-3-methylbutyl)-tetrazole
5-(1S-IPNC-Phe-His-AHCP-amino-3-methylbutyl)-tetrazole
5-(1S-MC-Phe-His-AHCP-amino-3-methylbutyl)-tetrazole 5-(1S-PBB-His-AHCP-amino-2S-methylbutyl)-tetrazole, M.p. 162°
5-(1S-PBB-His-AHCP-amino-3-methylbutyl)-tetrazole, M.p. 120°
5-(ETOC-Phe-His-AHCP-Ile-aminomethyl)-tetrazole
5-(IPOC-Phe-His-AHCP-Ile-aminomethyl)-tetrazole, M.p. 185°-190°(dec.)
5-(BOC-Phe-His-AHCP-Ile-aminomethyl)-tetrazole, M.p. 167°
5-(ETNC-Phe-His-AHCP-Ile-aminomethyl)-tetrazole
5-(IPNC-Phe-His-AHCP-Ile-aminomethyl)-tetrazole
5-(MC-Phe-His-AHCP-Ile-aminomethyl)-tetrazole, M.p. 151°-154°

5-(PBB-His-AHCP-Ile-aminomethyl)-tetrazole, M.p. 160°-162°
5-(ETOC-Phe-His-AHCP-Leu-aminomethyl)-tetrazole
5-(IPOC-Phe-His-AHCP-Leu-aminomethyl)-tetrazole
5-(BOC-Phe-His-AHCP-Leu-aminomethyl)-tetrazole, M.p. 189° (decomposition)
5-(ETNC-Phe-His-AHCP-Leu-aminomethyl)-tetrazole
5-(IPNC-Phe-His-AHCP-Leu-aminomethyl)-tetrazole
5-(MC-Phe-His-AHCP-Leu-aminomethyl)-tetrazole 5-(BOC-Phe-His-AHCH-Leu-aminomethyl)-tetrazole
5-(BOC-Phe-His-Sta-Leu-aminomethyl)-tetrazole
5-(BOC-Phe-His-AHPP-Leu-aminomethyl)-tetrazole
5-(BOC-Phe-His-DACP-Leu-aminomethyl)-tetrazole
5-(BOC-Phe-His-DACH-Leu-aminomethyl)-tetrazole
5-(BOC-Phe-His-DAMH-Leu-aminomethyl)-tetrazole
5-(BOC-Phe-His-DAPP-Leu-aminomethyl)-tetrazole 5-(CBZ-Phe-His-AHCP-Leu-aminomethyl)-tetrazole
5-(POA-Phe-His-AHCP-Leu-aminomethyl)-tetrazole

EXAMPLE 2

1 g of 2-amino-4-[1S-BOC-Phe-(imi-BOM-His)-AHCP-amino-3-methylbutyl]-thiazole [obtainable from 2-amino-4-(1S-H-AHCP-amino-3-methylbutyl)-thiazole and BOC-Phe-(imi-BOM-His)-OH] is dissolved in 10 ml of methanol and hydrogenated over 0.5% Pd-on-C at 20° and 1 bar until absorption ceases, the mixture is filtered and the filtrate is evaporated to give 2-amino-4-(1S-BOC-Phe-His-AHCP-amino-3-methylbutyl)-thiazole, M.p. 164°-166°.

The compounds indicated in Example 1 are obtained analogously from the corresponding imi-BOM derivatives.

EXAMPLE 3

A solution of 1 g of 2-(N'-m-nitrophenylureido)-4-(1S-BOC-Phe-His-AHCP-amino-2S-methylbutyl)-thiazole [M.p. 165° (decomposition); obtainable by reacting 2-amino-4-[1S-BOC-Phe(imi-DNP-His)-AHCP-amino-2S-methylbutyl]-thiazole with m-nitrophenyl isocyanate to give 2-(N'-m-nitrophenylureido)-4-[1S-BOC-Phe-(imi-DNP-His)-AHCP-amino-2S-methylbutyl]-thiazole and subsequently splitting off the imi-DNP group analogously to Example 1] in 50 ml of methanol is hydrogenated over 1 g of 5% Pd-on-C at 20° and 1 bar until absorption ceases. The mixture is filtered and the filtrate is evaporated to give 2-(N'-m-aminophenylureido)-4-(1S-BOC-Phe-His-AHCP-amino-2S-methylbutyl)-thiazole, M.p. 178° (decomposition).

EXAMPLE 4

1.01 g of N-methylmorpholine are added to a solution of 3.82 g of 2-amino-4-(1S-AHCP-amino-3-methylbutyl)-thiazole in 60 ml of methylene dichloride. 3.78 g of BOC-Phe-Nle-OH, 1.35 g of HOBt and a solution of 2.06 g of DCCI in 50 ml of methylene dichloride are added with stirring, the mixture is stirred for a further 14 hours at 4°, the precipitated dicyclohexylurea is filtered off and the filtrate is evaporated. Working up in a customary manner gives 2-amino-4-(1S-BOC-Phe-Nle-AHCP-amino-3-methylbutyl)-thiazole.

The following are obtained analogously from the corresponding BOC-dipeptides and 5-(1H-AHCP-Ile-aminomethyl)-tetrazole:
5-BOC-Phe-Abu-AHCP-Ile-aminomethyl)-tetrazole
5-(1S-BOC-Phe-Ada-AHCP-Ile-aminomethyl)-tetrazole
5-(1S-BOC-Phe-Ala-AHCP-Ile-aminomethyl)-tetrazole
5-(1S-BOC-Phe-Bia-AHCP-Ile-aminomethyl)-tetrazole
5-(1S-BOC-Phe-Cal-AHCP-Ile-aminomethyl)-tetrazole
5-(1S-BOC-Phe-Gln-AHCP-Ile-aminomethyl)-tetrazole
5-(1S-BOC-Phe-N-(im)-methyl-His-AHCP-Ile-aminomethyl)-tetrazole
5-(1S-BOC-Phe-Ile-AHCP-Ile-aminomethyl)-tetrazole
5-(1S-BOC-Phe-Leu-AHCP-Ile-aminomethyl)-tetrazole
5-(1S-BOC-Phe-tert.-Leu-AHCP-Ile-aminomethyl)-tetrazole
5-(1S-BOC-Phe-Met-AHCP-Ile-aminomethyl)-tetrazole
5-(1S-BOC-Phe-αNal-AHCP-Ile-aminomethyl)-tetrazole
5-(1S-BOC-Phe-βNal-AHCP-Ile-aminomethyl)-tetrazole
5-(1S-BOC-Phe-Nbg-AHCP-Ile-aminomethyl)-tetrazole 5-(1S-BOC-Phe-Nle-AHCP-Ile-aminomethyl)-tetrazole
5-(1S-BOC-Phe-Pro-AHCP-Ile-aminomethyl)-tetrazole
5-(1S-BOC-Phe-Ser-AHCP-Ile-aminomethyl)-tetrazole
5-(1S-BOC-Phe-Thr-AHCP-Ile-aminomethyl)-tetrazole
5-(1S-BOC-Phe-Tic-AHCP-Ile-aminomethyl)-tetrazole
5-(1S-BOC-Phe-Trp-AHCP-Ile-aminomethyl)-tetrazole
5-(1S-GOC-Phe-Val-AHCP-Ile-aminomethyl)-tetrazole

EXAMPLE 5

5-(BOC-Phe-Nle-AHCP-aminomethyl)-tetrazole is obtained, analogously to Example 4, from BOC-Phe-OH and 5-(H-Nle-AHCP-aminomethyl)-tetrazole [obtainable by reacting BOC-aminoacetonitrile with NaN$_3$ in DMF in the presence of NH$_4$Cl at 80°–90° to give 5-BOC-aminomethyltetrazole (M.p. 153°–155°), splitting off the BOC group to give 5-aminomethyltetrazole, subjecting the latter to a condensation reaction with BOC-Nle-AHCP-OH to give 5-BOC-Nle-AHCP-aminomethyltetrazole and again splitting off the BOC group].

EXAMPLE 6

2-Amino-4-(1S-BOC-Phe-Nle-AHCP-Ile-amino-3-methylbutyl)-thiazole is obtained, analogously to Example 4, from BOC-Phe-Nle-AHCP-OH and 2-amino-4-(1S-Ile-amino-3-methylbutyl)-thiazole.

EXAMPLE 7

2-Amino-4-(1S-BOC-Phe-Nle-AHCP-Ile-amino-3-methylbutyl)-thiazole is obtained, analogously to Example 4, from BOC-Phe-Nle-AHCP-Ile-OH and 2-amino-4-(1S-amino-3-methylbutyl)-thiazole.

EXAMPLE 8

A solution of 1 g of 2-amino-4-(1S-BOC-Phe-His-AHCP-amino-3-methylbutyl)-thiazole in 20 ml of 4 N HCl in dioxane is stirred for 30 minutes at 20° and is then evaporated. This gives 2-amino-4-(1S-H-Phe-His-AHCP-amino-3-methylbutyl)-thiazole.

The following are obtained analogously by scission from the corresponding N-BOC derivatives:
2-amino-4-(1S-H-Phe-His-AHCP-amino-2S-methylbutyl)-thiazole
2-N'-ethylureido-4-(1S-H-Phe-His-AHCP-amino-2S-methylbutyl)-thiazole
2-(1S-H-Phe-His-AHCP-amino-2S-methylbutyl)-4-ethoxycarbonyl-thiazole
2-(1S-H-Phe-His-AHCP-amino-3-methylbutyl)-4-N-(3-pyridylmethyl)-carbamoylthiazole
5-(H-Phe-His-AHCP-Leu-aminomethyl)-tetrazole.

EXAMPLE 9

1 g of 5-(CBZ-Phe-His-AHCP-aminomethyl)-tetrazole is dissolved in 10 ml of ethanol and hydrogenated over 0.5 g of 10% Pd-on-C at 20° and 1 bar for 3 hours, the mixture is filtered and the filtrate is evaporated to give, after purification by chromatography, 5-(H-Phe-His-AHCP-aminomethyl)-tetrazole.

The following are obtained analogously:
5-(1S-BOC-Phe-Dab-AHCP-Ile-aminomethyl)-tetrazole from
5-[1S-BOC-Phe-(4-CBZ-Dab)-AHCP-Ile-aminomethyl]-tetrazole;
5-(1S-BOC-Phe-Orn-AHCP-Ile-aminomethyl)-tetrazole from
5-[1S-BOC-Phe-(5-CBZ-Orn)-AHCP-Ile-aminomethyl]-tetrazole; and
5-(1S-BOC-Phe-Lys-AHCP-Ile-aminomethyl)-tetrazole from
5-[1S-BOC-Phe-(6-CBZ-Lys)-AHCP-Ile-aminomethyl]-tetrazole.

EXAMPLE 10

70 mg of hydroxylamine hydrochloride are added to a solution of 764 mg of 2-amino-4-[1S-(3-oxo-4S-BOC-Phe-His-amino-5-cyclohexylpentanoylamino)-3-methylbutyl]-thiazole and 1.43 g of Na$_2$CO$_3$. 10H$_2$O in 5 ml of methanol and 5 ml of methanol and 5 ml of water, and the mixture is stirred for 14 hours at 20°. The precipitated oxime is filtered off, dried, dissolved in 10 ml of methanol and hydrogenated over 0.5 g of Raney Ni at 20° and 5 bar. The catalyst is filtered off, the filtrate is evaporated and separation is carried out over silica gel (methylene dichloride/methanol/acetic acid/water) to give 2-amino-4-[1S-(3S-amino-4S-BOC-Phe-His-amino-5-cyclohexylpentanoylamino)-3-methylbutyl]-thiazole ["2-amino-4-(1S-BOC-Phe-His-DACP-amino-3-methylbutyl)-thiazole"]; the 3R-aminoepimer is obtained additionally.

EXAMPLE 11

Analogously to Example 1 (or (2), there are obtained by cleavage of the corresponding imi-DNP- (or imi -BOM) derivatives:
5-(BOC-Abu-His-AHCP-aminomethyl)-tetrazole
5-(BOC-Ada-His-AHCP-aminomethyl)-tetrazole
5-(BOC-Ala-His-AHCP-aminomethyl)-tetrazole
5-(BOC-Bia-His-AHCP-aminomethyl)-tetrazole
5-(BOC-Cal-His-AHCP-aminomethyl)-tetrazole
5-(BOC-Met-His-AHCP-aminomethyl)-tetrazole
5-(BOC-αNal-His-AHCP-aminomethyl)-tetrazole
5-(BOC-Nle-His-AHCP-aminomethyl)-tetrazole
5-(BOC-Phe-His-AHCP-aminomethyl)-tetrazole
5-(BOC-Trp-His-AHCP-aminomethyl)-tetrazole
5[(2-benzylheptanoyl)-His-AHCP-Ile-aminomethyl]-tetrazole, M.p. 169°–171°
5-(morpholinoacetyl-Phe-His-AHCP-Ile-aminomethyl)-tetrazole, M.p. 187°–190°
5-[2-(2-pyridyl)-ethoxycarbonyl-Phe-His-AHCP-Ile-aminomethyl]-tetrazole, M.p. 150° (dec.).
5-(pyrrolidinoacetyl-Phe-His-AHCP-Ile-aminomethyl)-tetrazole
5-(piperidinoacetyl-Phe-His-AHCP-Ile-aminomethyl)-tetrazole
5-(thiomorpholinoacetyl-Phe-His-AHCP-Ile-aminomethyl)-tetrazole
5-(BOC-Pro-Phe-His-AHCP-Ile-aminomethyl)-tetrazole
5-(N-benzyl-N-isopentyl-carbamoyl-His-AHCP-Ile-aminomethyl)-tetrazole
5-(BOC-Phe-his-HACP-Ile-amino)-tetrazole
5-[2-(BOC-Phe-AHCP-Ile-amino)-ethyl]-tetrazole
5-(dibenzylacetyl-His-AHCP-Ile-aminomethyl)-tetrazole
5-(dibenzylacetyl-His-Sta-Ile-aminomethyl)-tetrazole
5-[2-benzyl-3-(1-naphthyl)-propionyl-His-AHCP-Ile-aminomethyl]-tetrazole
5-[2-benzyl-3-(1-naphthyl)-propionyl-His-Sta-Ile-aminomethyl]-tetrazole
5-[bis-(1-naphthylmethyl)-acetyl-His-AHCP-Ile-aminomethyl]-tetrazole
5-bis-(1-naphthylmethyl)-acetyl-His-Sta-Ile-aminomethyl)-tetrazole 5-[2-isopropyl-4S-hydroxy-5S-(BOC-Phe-His-amino)-6-cyclohexyl-hexanoyl-Ile-aminomethyl]-tetrazole 5-[2-isopropyl-4S-hydroxy-5S-(IPOC-Phe-His-amino)-6-cyclohexyl-hexanoyl-Ile-aminomethyl]-tetrazole 5-[2-isopropyl-4S-hydroxy-5S-(morpholinoacetyl-Phe-His-amino)-6-cyclohexyl-hexanoyl-Ile-aminomethyl]-tetrazole 5-[2-isopropyl-4S-hydroxy-5S-((2-benzylheptanoyl)-Phe-His-amino)-6-cyclohexyl-hexanoyl-Ile-aminomethyl]-tetrazole 5-[2-isopropyl-4S-hydroxy-5S-(N-benzyl-n-butyl-carbamoyl)-Phe-His-amino)-6-cyclohexyl-hexanoyl-Ile-aminomethyl]-tetrazole 5-[2-isopropyl-4S-hydroxy-5S-(N-benzyl-n-isopentyl-carbamoyl)-Phe-His-amino)-6-cyclohexyl-hexanoyl-Ile-aminomethyl]-tetrazole 5-[2-isopropyl-4S-hydroxy-5S-(bis-(1-naphthylmethyl)-acetyl-His-amino-6-cyclohexyl-hexanoyl-Ile-aminomethy]-tetrazole 5-[2-isopropyl-4S-hydroxy-5S-(BOC-Phe-His-amino)-7-methyl-heptanoyl-Ile-aminomethyl]-tetrazole 5-[2-isopropyl-4S-hydroxy-5S-(morpholinoacetyl-Phe-His-amino)-7-methyl-heptanoyl-Ile-aminomethyl]-tetrazole 5-[2-isopropyl-4S-hydroxy-5S-(N-benzyl-n-butyl-carbamoyl)-Phe-His-amino)-7-methyl-heptanoyl-Ile-aminomethyl]-tetrazole.

The examples below relate to pharmaceutical formulations.

Example A: Vials

The pH of a solution of 100 g of 2-amino-4-(1S-BOC-Phe-His-AHCP-amino-3-methylbutyl)-thiazole and 5 g of disodium hydrogen-phosphate in 3 liters of twice-distilled water is adjusted to 6.5 with 2N hydrochloric acid, and the mixture is filtered under sterile conditions, filled into vials, lyophilized under sterile conditions and sealed in a sterile manner. Each vial contains 500 mg of active compound.

Example B: Suppositories

A mixture of 500 g of 5-(BOC-Phe-His-AHCP-Leu-aminomethyl)-tetrazole and 100 g of soya lecithin and 1400 g of cocoa butter is melted, poured into moulds and allowed to cool. Each suppository contains 500 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An amino acid derivative of the formula

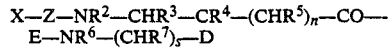

wherein

X is H, $R^1$—O—$C_mH_{2m}$—CO—, $R^1$—$C_mH_{2m}$—O—CO—, $R^1$—$C_mH_{2m}$—CO—, $R^1$—$SO_2$— or ($R^1$—$C_m$—$H_{2m}$)—L($R^1$—$C_pH_{2p}$)—$C_rH_{2r}$—CO—;

Z is 0 to 4 amino acid radicals attached to one another by a peptide linkage and selected from Abu, Ada, Ala, Arg, Asn, Asp, Bia, Cal, Dab, Gln, Glu, His, N(im)-Alkyl-His, Ile, Leu, tert.-Leu, Lys, Met, Nal, βNal, Nbg, Nle, Orn, Phe, Pro, Ser. Thr, Tic, Trp, Tyr or Val;

E is 0 to 2 amino acid radicals attached to one another by a peptide linkage and selected from Abu, Ala, Cal, His, Ile, Leu, Met, Nle, Phe, Trp, Tyr or Val;

D is a tetrazolyl group which is unsubstituted or substituted by A or a thiazolyl group which is substituted by $H_2N$, HAN, $A_2N$, $R^8$—CO—NH—, $R^9$—NH—CO—NH—, $R^{10}$—NH—CS—NH—, $R^{11}$OOC—, $R^{12}R^{13}$N—CO— or CN;

$R^1$, $R^3$, $R^7$, $R^8$, $R^9$, $R^{10}$, $R^{11}$, $R^{12}$ and $R^{13}$ are each independently H, A, Ar, Ar-alkyl wherein the alkyl residue has 1-8 C atoms, Het, Het-alkyl wherein the alkyl residue has 1-8 C atoms, cycloalkyl which has 3-7 C atoms and is unsubstituted or monosubstituted or polysubstituted by A, AO or Hal or a combination thereof, cycloalkylalkyl having 4-11 C atoms, bicycloalkyl or tricycloalkyl having in each case 7-14 C atoms or bicycloalkylalkyl or tricycloalkylalkyl having in each case 8-18 C atoms;

$R^2$, $R^5$, and $R^6$ independently are each H or A;

$R^4$ is (H, OH), (H, $NH_2$) or =O;

L is CH or N;

m, p and r are each independently 0, 1, 2, 3, 4 or 5;

n is 1 or 2;

s is 0, 1 or 2;

Ar is phenyl which is unsubstituted or monosubstituted or polysubstituted by A, AO, Hal, $CF_3$, OH, $NH_2$ or a combination thereof, or is unsubstituted naphthyl;

Het is a saturated or unsaturated, 5-membered or 6-membered, heterocyclic radical which has 1-4 N, O or S atoms or a combination thereof, and which can be condensed with a benzene ring, and optionally monosubstituted or polysubstituted by A, AO, Hal, $CF_3$, HO, $O_2N$, carbonyl oxygen, $H_2N$, HAN, $A_2N$, AcNH, AS, ASO, $ASO_2$, AOOC, CN, $H_2NCO$, $H_2NSO_2$, $ASO_2NH$, Ar, Ar-alkenyl wherein the alkenyl residue has 2-8 C atoms, hydroxyalkyl having 1-8 C atoms, or aminoalkyl having 1-8 C atoms, or a combination thereof, and the N and S heteroatoms can independently optionally be oxidized;

Hal is F, Cl, Br or I;

Ac is A—CO—, Ar—CO— or A—NH—CO— and

A is alkyl having 1-8 C atoms; and wherein one or more —N(alkyl—CO— groups can also be present instead of one or more —NH—CO— groups, or a physiologically acceptable salt thereof.

2. An amino acid derivative according to claim 1, wherein

X is H, ETOC, IPOC, BOC, POA, CBZ, ETNC, IPNC, MC, 2-phenylbutyryl, 2-benzyl-3-phenylpropionyl, PBB, 2-(2-phenylethyl)-4-phenylbutyryl or 2-(2-naphthylmethyl)-4-phenylbutyryl, Z is absent or is His, Ada-His, Cal-His, αNal-His, βNal-His, Phe-Abu, Phe-Bia, Phe-Dab, Phe-His, Phe-N(im)-methyl-His, Phe-Leu, Phe-Lys, Phe-Met, Phe-Nle, or Phe-Orn, $R^2$ and $R^5$ are H, $R^3$ is isobutyl, cyclohexylmethyl, 2-cyclohexylethyl or benzyl, n and s are each 1, E is absent or is Ile or Leu, R$^7$ is H or alkyl having 1-4 C atoms and D is 2-amino-4-thiazolyl, 2-(R$^8$-CO—NH)-4-thiazolyl, 2-(R$^9$-NH-CO-NH)-4-thiazolyl, 4-(R$^{11}$OOC)-2-thiazolyl, 4-(R$^{12}$-R$^{13}$N-CO)-2-thiazolyl or 5-tetrazolyl.

3. An amino acid derivative according to claim 1, wherein

X is H, ETOC, IPOC, BOC, ETNC, IPNC, MC or PBB,

Z is His, Ada-His, Cal-His, α-Nal-His, β-Nal-His, Phe-Abu, Phe-Bia, Phe-Dab, Phe-His, Phe-N(im)-methyl-His, Phe-Leu, Phe-Lys, Phe-Met, Phe-Nle or Phe-Orn, R$^2$ and R$^5$ are H, R$^3$ is cyclohexylmethyl, R$^4$ is (H, OH), n and s are each 1, E is absent or is Ile or Leu, R$^7$ is H or alkyl having 1-4 C atoms, D is 2-amino-4-thiazolyl, 2-(R$^8$-CO-NH)-4-thiazolyl, 2-(R$^9$-NH-CO-NH)-4-thiazolyl, 4-(R$^{11}$OOC)-2-thiazolyl, 4-(R$^{12}$R$^{13}$N-CO)-2-thiazolyl or 5-tetrazolyl R$^8$ is H, A, phenyl or pyridyl, R$^9$ is H, A, phenyl or aminophenyl, R$^{11}$ is A, R$^{12}$ is H, A, phenyl or pyridylmethyl and R$^{13}$ is H.

4. An amino acid derivative according to claim 1, wherein

X is BOC, PBB or MC,

Z is His or Phe-His,

R$^2$ and R$^5$ are each H,

R$^3$ is cyclohexylmethyl,

R$^4$ is (H, OH), n and s are each 1,

E is absent or is Ile or Leu,

R$^7$ is H, isobutyl or sec.-butyl and

D is 2-amino-4-thiazolyl, 2-N'-ethylureido-4-thiazolyl, 2-N'-m-aminophenylureido-4-thiazolyl, 4-ethoxycarbonyl-2-thiazolyl or 4-N'-(3-pyridylmethyl)-carbamoyl-2-thiazolyl.

5. An amino acid derivative according to claim 1, wherein D is 5-tetrazolyl.

6. An amino acid derivative according to claim 2 wherein D is 5-tetrazolyl.

7. An amino acid derivative according to claim 3, wherein D is 5-tetrazolyl.

8. An amino acid derivative according to claim 1, wherein

X is BOC, PBB or MC,

Z is His or Phe-His,

R$^2$ and R$^5$ are each H,

R$^3$ is cyclohexylmethyl,

R$^4$ is (H, OH), n and s are each 1,

E is absent or is Ile or Leu,

R$^7$ is H, isobutyl or sec.-butyl 9.
(a) 2-Amino-4-(1S-BOC-Phe-His-AHCP-amino-3-methyl-butyl)-thiazole;
(b) 2-amino-4-[1S-(2-benzyl-4-phenylbutyryl-His-AHCP-amino)-3-methylbutyl]-thiazole;
(c) 5-(BOC-Phe-His-AHCP-Leu-aminomethyl)-tetrazole;
(d) 5-(BOC-Phe-His-AHCP-Ile-aminomethyl)-tetrazole;
(e) 5-(2-benzyl-4-phenylbutyryl-His-AHCP-Ile-aminomethyl)-tetrazole;
(f) 5-(morpholinocarbonyl-Phe-His-AHCP-Ile-aminomethyl)-tetrazole, each a compound of claim 1.

10. A pharmaceutical composition comprising a compound of claim 1 and a pharmaceutically acceptable carrier.

11. A pharmaceutical composition comprising about 100 mg to 30 g of a compound of claim 1 and a pharmaceutically acceptable carrier.

12. A pharmaceutical composition comprising about 500 mg to 5 g of a compound of claim 1 and a pharmaceutically acceptable carrier.

13. A method of treating renin-dependent hypertension comprising administering a compound of claim 1.

14. A method according to claim 13, comprising administering doses of said compound in an amount of about 1 to 300 mg/kg of body weight.

15. A method for treating hyperaldosteronism comprising administering a compound of claim 1.

16. A method according to claim 15, comprising administering doses of said compound in an amount of about 1 to 300 mg/kg of body weight.

17. A method of treating cardiac insufficiency comprising administering a compound of claim 1.

18. A method of treating or prophylaxis of hypertension, cardiac insufficiency or hyperaldosteronism comprising administering a compound of claim 1.

* * * * *

UNITED STATES PATENT AND TRADEMARK OFFICE
CERTIFICATE OF CORRECTION

PATENT NO. : 4,829,053
DATED : May 9, 1989
INVENTOR(S) : Peter Raddatz et al

It is certified that error appears in the above-identified patent and that said Letters Patent is hereby corrected as shown below:

Column 32, line 3: reads "Nal, βNal, Nbg, Nle, Orn, Phe, Pro, Ser. Thr, Tic,"

should read -- Nal, βNal, Nbg, Nle, Orn, Phe, Pro, Ser, Thr, Tic, --

Column 32, line 50: reads "wherein one or more-N(alkyl-CO-groups can also"

should read -- wherein one or more-N(alkyl)-CO-groups can also --

Signed and Sealed this

Fifth Day of December, 1989

Attest:

JEFFREY M. SAMUELS

*Attesting Officer*     *Acting Commissioner of Patents and Trademarks*